(12) United States Patent
Nagorny et al.

(10) Patent No.: US 10,565,015 B2
(45) Date of Patent: Feb. 18, 2020

(54) SPIROKETAL-BASED C2-SYMMETRIC SCAFFOLD FOR ASYMMETRIC CATALYSIS

(71) Applicant: THE REGENTS OF THE UNIVERSITY OF MICHIGAN, Ann Arbor, MI (US)

(72) Inventors: Pavel Nagorny, Ann Arbor, MI (US); Siyuan Sun, Ann Arbor, MI (US); Alonso Arguelles, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/134,568

(22) Filed: Sep. 18, 2018

(65) Prior Publication Data

US 2019/0084995 A1    Mar. 21, 2019

Related U.S. Application Data

(60) Provisional application No. 62/559,903, filed on Sep. 18, 2017.

(51) Int. Cl.

| C07F 15/00 | (2006.01) |
| C07F 9/6571 | (2006.01) |
| B01J 31/24 | (2006.01) |
| C07F 9/6561 | (2006.01) |
| G06F 9/50 | (2006.01) |
| G06F 11/30 | (2006.01) |
| G06F 9/48 | (2006.01) |
| C07C 2/86 | (2006.01) |
| C07C 67/343 | (2006.01) |
| C07D 213/30 | (2006.01) |
| C07D 215/06 | (2006.01) |
| C07D 493/10 | (2006.01) |

(52) U.S. Cl.
CPC ........ *G06F 9/5022* (2013.01); *B01J 31/2452* (2013.01); *C07C 2/868* (2013.01); *C07C 67/343* (2013.01); *C07D 213/30* (2013.01); *C07D 215/06* (2013.01); *C07D 493/10* (2013.01); *C07F 9/6561* (2013.01); *C07F 9/657154* (2013.01); *C07F 15/006* (2013.01); *C07F 15/0033* (2013.01); *G06F 9/485* (2013.01); *G06F 9/5016* (2013.01); *G06F 11/3037* (2013.01); *B01J 2231/32* (2013.01); *B01J 2231/4261* (2013.01); *B01J 2231/44* (2013.01); *B01J 2231/646* (2013.01); *B01J 2531/824* (2013.01); *B01J 2531/827* (2013.01); *C07C 2603/86* (2017.05); *G06F 2201/81* (2013.01)

(58) Field of Classification Search
CPC .................................................... C07F 9/6561
See application file for complete search history.

(56) References Cited

U.S. PATENT DOCUMENTS

| 2006/0091357 A1 | 5/2006 | Welter et al. |
| 2013/0063693 A1 | 3/2013 | Cheng et al. |
| 2013/0135574 A1 | 5/2013 | Wang et al. |

FOREIGN PATENT DOCUMENTS

| CN | 1439643 A | 9/2003 |
| CN | 1760198 A | 4/2006 |
| CN | 1884290 A | 12/2006 |
| CN | 1887893 A | 1/2007 |
| CN | 102030780 A | 4/2011 |
| CN | 103087106 A | 5/2013 |
| CN | 105327121 A | 2/2016 |

(Continued)

OTHER PUBLICATIONS

Birman et al., 1,1'-Spirobiindane-7,7'-diol: a novel, C2-symmetric chiral ligand, Tetrahedron: Asymmetry, 1091):125-31 (Jan. 1999).

(Continued)

*Primary Examiner* — Noble E Jarrell

(74) *Attorney, Agent, or Firm* — Marshall, Gerstein & Borun LLP

(57) ABSTRACT

Provided herein is a compound of formula (I):

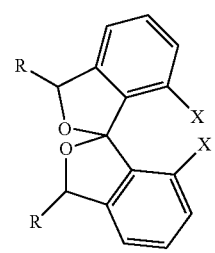

wherein each R is independently selected from the group consisting of $C_{1-8}$ alkyl, $C_{1-8}$ heteroalkyl having 1-4 heteroatoms independently selected from N, O, and S, $C_{3-6}$ cycloalkyl, 3-10 membered heterocycloalkyl having 1-4 heteroatoms independently selected from N, O, and S, $C_{6-10}$ aryl, and 5-10 membered heteroaryl having 1-4 heteroatoms independently selected from N, O, and S; each X is independently selected from OH, $PAr_2$, $P(O)Ar_2$, $OPAr_2$, $C_{3-6}$ cycloalkyl, 3-10 membered heterocycloalkyl having 1-4 heteroatoms independently selected from N, O, and S or each X together form $O_2PNR'_2$; Ar is $C_{6-10}$aryl; and each R' is independently selected from hydrogen and $C_{1-8}$ alkyl. Also provided are methods of making and using the compound of formula (I).

24 Claims, 2 Drawing Sheets

(56) References Cited

FOREIGN PATENT DOCUMENTS

| CN | 105503542 A | 4/2016 |
|---|---|---|
| JP | 2005283370 A | 10/2005 |
| JP | 2006070001 A | 3/2006 |
| WO | WO-2005/023742 A2 | 3/2005 |
| WO | WO-2014/196920 A1 | 12/2014 |
| WO | WO-2014/196930 A1 | 12/2014 |

OTHER PUBLICATIONS

Chiral Catalysts & Ligands, Daicel Chiral Technologies (China) Co., Ltd., downloaded from the Internet at: <http://www.daicelchiraltech.cn/reagents/list02.aspx?pid=72057594037927936&cid=77124143618719744> (published before Sep. 2017).

Coric et al., Kinetic resolution of homoaldols via catalytic asymmetric transacetalization, J. Am. Chem. Soc., 132(49):17370-3 (Dec. 2010).

Ding et al., Spiro skeletons: a class of privileged structure for chiral ligand design, Chem. Asian J., 4(1):32-41 (Jan. 2009).

Dubinnyi et al., Novel peptide chemistry in terrestrial animals: natural luciferin analogues from the bioluminescent earthworm Fridericia heliota, Chemistry, 21(10):3942-7 (Mar. 2015).

Ebe et al., Iridium-Catalyzed Regio- and Enantioselective Hydroarylation of Alkenyl Ethers by Olefin Isomerization, Angew. Chem. Int. Ed. Engl., 56(20):5607-11 (May 2017).

Gao et al., Base-promoted [1,4]-Wittig rearrangement of chalcone-derived allylic ethers leading to aromatic β-benzyl ketones, RSC Adv., 43(5):33818-22 (2015).

Hu et al., Palladium-catalyzed asymmetric intermolecular cyclization, Angew. Chem. Int. Ed. Engl., 52(33):8676-80 (Aug. 2013).

Matsubara et al., Nickel-catalyzed allylic substitution of simple alkenes, J. Am. Chem. Soc., 132(20):6880-1 (May 2010).

Noyori, Asymmetric catalysis: science and opportunities (Nobel lecture), Angew. Chem. Int. Ed. Engl., 41(12):2008-22 (Jun. 2002).

Tang et al., Asymmetric hydrogenation of quinolines with high substrate/catalyst ratio, Chem. Commun. (Camb), (6):613-5 (Feb. 2007).

Xie et al., Application of SDP Ligands for Pd-Catalyzed Allylic Alkylation, Adv. Synth. Catal., 346(6):625-32 (2004).

Xie et al., Synthesis of spiro diphosphines and their application in asymmetric hydrogenation of ketones, J. Am. Chem. Soc., 125(15):4404-5 (Apr. 2003).

Xu et al., SPINOL-derived phosphoric acids: synthesis and application in enantioselective Friedel-Crafts reaction of indoles with imines, J. Org. Chem., 75(24):8677-80 (Dec. 2010).

(R,S,S)/(S,R,R)-diastereomers:

(R,R,R)/(S,S,S)-diastereomers:

SPIROKETAL-BASED C2-SYMMETRIC SCAFFOLD FOR ASYMMETRIC CATALYSIS

STATEMENT OF GOVERNMENT SUPPORT

This invention was made with government support under grant numbers CHE-1350060 awarded by the National Science Foundation. The government has certain rights in the invention.

FIELD OF THE DISCLOSURE

The disclosure relates to scaffolds for asymmetric catalysis and, more specifically, relates to a spiroketal-based C2-symmetric scaffold for asymmetric catalysis.

BACKGROUND

Driven by the fact that the majority of key molecules in biological systems are chiral, and thus most enantiomers of drugs showcase marked differences in biological activities, the demand for the preparation of chiral compounds in enantiopure form is ever increasing. For this reason, the development of versatile and efficient synthetic tools for the construction of asymmetric building blocks is of paramount importance in current modern Organic Chemistry. One of the most efficient ways of enantioselectively constructing molecules is by asymmetric organometallic catalysis, where the unique reactivity of transition metals is exploited in the context of enantioselective reactions using appropriate chiral ligands. Since the level of enantiocontrol is largely determined by the ligand employed, the development of new chiral ligands is of utmost importance in the field of asymmetric synthesis.

By far, the most popular ligand for this purpose has been the 1,1'-Bi-2-naphthol (BINOL)-derived diphosphine (BINAP). This was established in the 80s by Nobel Laureate Ryoji Noyori as a remarkably efficient ligand for Rh and Ru-catalyzed asymmetric hydrogenations and was instrumental in popularizing the field of asymmetric organometallic catalysis. Being widely regarded as a privileged scaffold, BINAP has been used in countless unrelated reactions with excellent results. BINOL-derived ligands are not a panacea, however, as in many reactions their performance is unsatisfactory. For this reason, chemists in the field strive to develop new powerful and general ligands.

Acetal-containing ligands have been of great utility to asymmetric catalysis and several important scaffolds containing acetal functionality are depicted in FIG. 1. While the acetal functionality cannot withhold strongly acidic or Lewis acidic conditions, these functionalities are compatible with most of the reaction conditions traditionally employed in transition metal catalysis. Additionally, the presence of the oxygenation in the ligand backbone can affect the electronic and structural properties of the ligand, and the synthesis of such ligands could offer significant advantages over the preparation of similar carbon-substituted analogs. Not surprisingly, acetal-containing ligands are present in the list of products vendored by Strem (cf. FIG. 1) as well as other suppliers (Sigma, etc.).

In 1999, the synthesis of chiral 1,1-spirobiindane-7,7-diol (SPINOL, FIG. 1) was first reported by the Birman group. Following this, several derivatives were introduced in catalysis such as diphosphine ligands in 2003, and as phosphoric acids in 2010. Subsequently, the SPINOL core has been demonstrated to be exceptional in catalysis in many instances. However, despite the overwhelming success of the SPINOL scaffold, a major disadvantage of both SPINOL-derived catalysts and ligands, which explains their lack of popularity compared to other catalysts, is that their preparation is low yielding, costly, and involves a large number of steps, including a chiral resolution.

SUMMARY

One aspect of the disclosure provides compounds of formula (I):

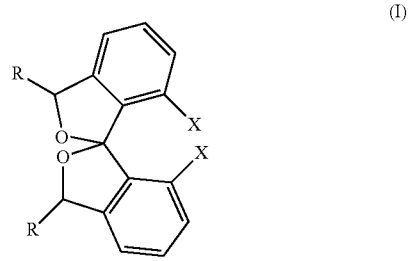

(I)

wherein each R is independently selected from the group consisting of $C_{1-8}$ alkyl, $C_{1-8}$ heteroalkyl having 1-4 heteroatoms independently selected from N, O, and S, $C_{3-6}$ cycloalkyl, 3-10 membered heterocycloalkyl having 1-4 heteroatoms independently selected from N, O, and S, $C_{6-10}$ aryl, and 5-10 membered heteroaryl having 1-4 heteroatoms independently selected from N, O, and S, each X is independently selected from OH, $PAr_2$, $P(O)Ar_2$, $OPAr_2$, $C_{3-6}$ cycloalkyl, 3-10 membered heterocycloalkyl having 1-4 heteroatoms independently selected from N, O, and S, $C_{6-10}$ aryl, and 5-10 membered heteroaryl having 1-4 heteroatoms independently selected from N, O, and S, or each X together form $O_2PNR'_2$, Ar is $C_{6-10}$ aryl, and each R' is independently selected from hydrogen and $C_{1-8}$ alkyl.

Another aspect of the disclosure provides a catalyst comprising a compound of formula (I) according to the disclosure and a transition metal.

Another aspect of the disclosure provides methods of forming a reaction products having a chiral center, the methods comprising admixing a first reactant, a second reactant, and the catalyst of the disclosure under conditions sufficient to allow reaction of the first reactant and the second reactant to form a reaction product, wherein the reaction product comprises a chiral center and the reaction produces an enantiomeric excess (ee) of the reaction product.

Yet another aspect of the disclosure provides preparing compound (S,S,S)-4:

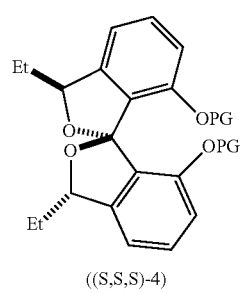

((S,S,S)-4)

the method comprising (a) cooling a solution of compound (S)-2:

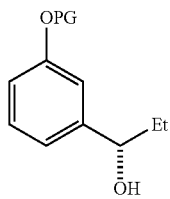

to 0° C., wherein PG is a hydroxy protecting group, (b) adding an organolithium reagent to the cooled solution of step (a) to form a mixture, (c) warming the mixture of step (b) to room temperature and keeping it at room temperature to dissolve suspended material and form a solution, (d) cooling the solution of step (c) to 0° C., (e) admixing the solution of step (d) and diethyl carbonate at 0° C. (f) warming the reaction mixture of step (e) to room temperature, and (g) admixing the reaction mixture of step (f) with acetic acid.

Yet another aspect of the disclosure provides a method of preparing compound (S,S,S)-8:

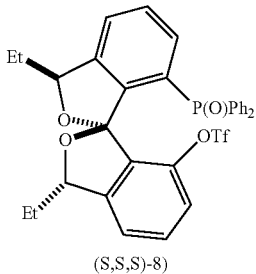

(S,S,S)-8 the method comprising admixing diphenylphosphine oxide with compound (S,S,S)-7 and, optionally, compound (S,R,S)-7 in the presence of a catalyst to form compound (S,S,S)-8, wherein the temperature of the admixing is 70° C. to 90° C.

Yet another aspect of the disclosure provides a method of preparing compound (R,S,S)-8:

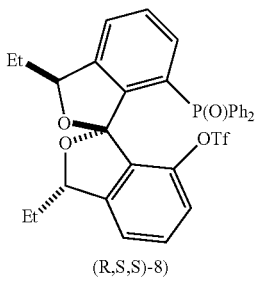

(R,S,S)-8 the method comprising admixing diphenylphosphine oxide with compound (R,S,S)-7 in the presence of a catalyst to form compound (R,S,S)-8, wherein the temperature of the admixing is 90° C. to 110° C.

DETAILED DESCRIPTION

Disclosed herein are compounds of formula (I):

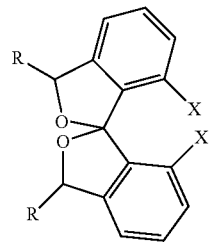

(I)

wherein each R is independently selected from the group consisting of $C_{1-8}$ alkyl, $C_{1-8}$ heteroalkyl having 1-4 heteroatoms independently selected from N, O, and S, $C_{3-6}$ cycloalkyl, 3-10 membered heterocycloalkyl having 1-4 heteroatoms independently selected from N, O, and S, $C_{6-10}$ aryl, and 5-10 membered heteroaryl having 1-4 heteroatoms independently selected from N, O, and S, each X is independently selected from OH, PAr$_2$, P(O)Ar$_2$, OPAr$_2$, $C_{3-6}$ cycloalkyl, 3-10 membered heterocycloalkyl having 1-4 heteroatoms independently selected from N, O, and S, $C_{6-10}$ aryl, and 5-10 membered heteroaryl having 1-4 heteroatoms independently selected from N, O, and S, or each X together form O$_2$PNR'$_2$, Ar is $C_{6-10}$ aryl, and each R' is independently selected from hydrogen and $C_{1-8}$ alkyl.

Figure 1A:
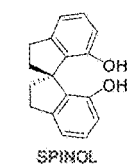
FIG. 1A shows the structure of a commercial ligand, SPINOL.
Figure 1B:
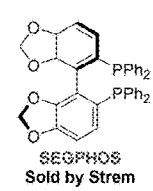
FIG. 1B shows the structure of commercial acetal-containing ligands SEGPHOS, (S,S,S)-SKP, and TADDOL.
Figure 1B:
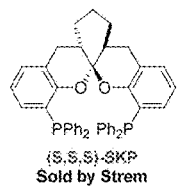
Figure 1C:
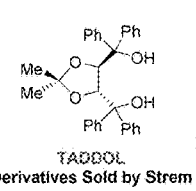
FIG. 1C shows the SPIROL ligand of the disclosure.
Figure 1C:
Figure 1D:
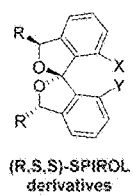
FIG. 1D shows the generic structures of (R,S,S)-SPIROL derivatives and (S,S,S)-SPIROL derivatives of the disclosure.
Figure 1D:
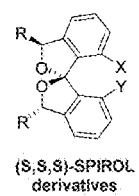

The compounds of the disclosures are scaffolds based on a chiral spiroketal analog of SPINOL, termed SPIROL (FIG. 1). The compounds of the disclosure are advantageous over SPINOL for one or more reasons, such as the substitution of the carbon-carbon bonds of SPINOL for carbon-oxygen bonds in SPIROL can allow for a short synthesis; the inclusion of fixed stereocenters in the benzylic position of SPIROL precludes the need for a chiral resolution; and the SPIROL ligands demonstrate excellent performance in one or more transformations, including, but not limited to asymmetric hydroarylation, asymmetric allylic alkylation, hydrogenation, and/or asymmetric intermolecular Heck reaction and domino cyclization.

SPIROL derivatives, a new type of spiroketal-based ligands, possess C2-symmetry and chirality, and the directionality of the C—X bonds (as well as overall 3D structure of the scaffold) is similar to the SPINOL-based backbone. Although SPINOL and SPIROL are similar in terms of the key structural features, these ligands are not completely identical due to oxygenation and two additional stereogenic centers present in SPIROL. Similar to TADDOL, SKP, and SEGPHOS (FIG. 1); the SPIROL scaffold is less stable to highly Brönsted acidic and strongly Lewis acidic conditions (in comparison to SPINOL), but is compatible with the majority of moderately acidic, neutral, and basic reactions conditions employed in transition metal catalysis. The introduction of the spiroacetal functionality and 2 additional substituents offers some advantages to SPIROL based scaffold. These advantages include significantly easier preparation; access to two distinct, pseudoenantiomeric, and configurationally stable subclasses of SPIROL ((R,S,S)- and (S,S,S)-SPIROL); and/or additional tunability due to the variation in R groups.

The compounds of the disclosure can be represented by formula (I):

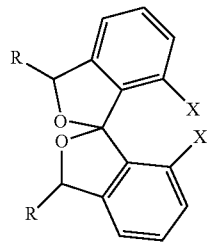

(I)

wherein each R is independently selected from the group consisting of $C_{1-8}$ alkyl, $C_{1-8}$ heteroalkyl having 1-4 heteroatoms independently selected from N, O, and S, $C_{3-6}$ cycloalkyl, 3-10 membered heterocycloalkyl having 1-4 heteroatoms independently selected from N, O, and S, $C_{6-10}$ aryl, and 5-10 membered heteroaryl having 1-4 heteroatoms independently selected from N, O, and S; each X is independently selected from OH, $PAr_2$, $P(O)Ar_2$, $OPAr_2$, $C_{3-6}$ cycloalkyl, 3-10 membered heterocycloalkyl having 1-4 heteroatoms independently selected from N, O, and S, or together form $O_2PNR'_2$; wherein Ar is $C_{6-10}$ aryl and each R' is independently selected from hydrogen and $C_{1-8}$ alkyl.

In embodiments, the compound of formula (I) can be a compound of formula (IA):

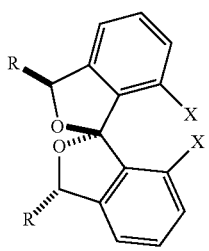

(IA)

wherein the compounds of formula (IA) are (R,S,S)-SPIROL derivatives.

In embodiments, the compound of formula (I) can be a compound of formula (IB):

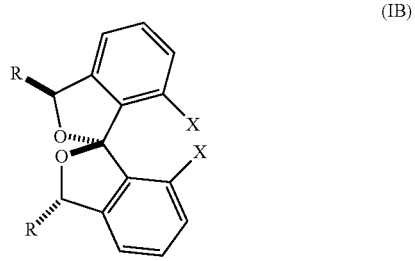

(IB)

wherein the compounds of formula (IB) are (S,S,S)-SPIROL derivatives.

X can be independently selected from OH, $PAr_2$, $P(O)Ar_2$, $OPAr_2$, $C_{3-6}$ cycloalkyl, 3-10 membered heterocycloalkyl having 1-4 heteroatoms independently selected from N, O, and S, or together form $O_2PNR'_2$ (i.e., form a structure of

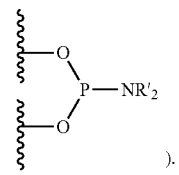

).

In some embodiments, at least one X is OH. In some embodiments, each X is OH. In some embodiments, at least one X is $PAr_2$. In refinements of the foregoing embodiment, one or both Ar can be phenyl. In some embodiments, both X are $PAr_2$. In refinements of the foregoing embodiment, one or both Ar can be phenyl. In embodiments, at least one X is $OPAr_2$. In refinements of the foregoing embodiment, one or both Ar can be phenyl. In some embodiments, both X are $OPAr_2$. In refinements of the foregoing embodiment, one or both Ar can be phenyl. In embodiments, at least one X is $P(O)Ar_2$. In refinements of the foregoing embodiment, one or both Ar can be phenyl. In some embodiments, both X are $P(O)Ar_2$. In refinements of the foregoing embodiment, one or both Ar can be phenyl. In some embodiments, one X can be $PAr_2$ and one X can be $P(O)Ar_2$. In refinements of the foregoing embodiments, one or more Ar can be phenyl. In some embodiments, one X can be $PAr_2$ and one X can $OPAr_2$. In refinements of the foregoing embodiments, one or more Ar can be phenyl. In some embodiments, one X can be $OPAr_2$ and one X can be $P(O)Ar_2$. In refinements of the foregoing embodiments, one or more Ar can be phenyl. In some embodiments, one X can be a 5-member heterocycle comprising one N atom and one O atom. In refinements of the foregoing embodiments, X can be 4,5-dihydrooxazole or 4,5-dihydrooxazole substituted with Ar. In some embodiments, both X can be 5-member heterocycles comprising one N atom and one O atom. In refinements of the foregoing embodiments, both X can be 4,5-dihydrooxazole or 4,5-dihydrooxazole substituted with Ar. In some embodiments, one or both X can be 4-phenyl-4,5-dihydrooxazole. In some embodiments, one X can be $PAr_2$ and one X can be 4,5-dihydrooxazole or 4,5-dihydrooxazole substituted with Ar. In some embodiments, one X can be $OPAr_2$ and one X can be 4,5-dihydrooxazole or 4,5-dihydrooxazole substituted with Ar. In some embodiments, one X can be P(O)Ar$_2$ and one X can be 4,5-dihydrooxazole or 4,5-dihydrooxazole substituted with Ar.

In some embodiments, both X together can form O$_2$PNR'$_2$. Each R' can independently be hydrogen or C$_{1-8}$ alkyl. In some embodiments, at least one R' can be hydrogen. In some embodiments, both R' can be hydrogen. In some embodiments, at least one R' can be a C$_{1-8}$ alkyl. In some embodiments, both R' can be C$_{1-8}$ alkyl. In some embodiments, one R' can hydrogen and one R' can C$_{1-8}$ alkyl. In some embodiments, at least one R' can be methyl. In some embodiments, both R' can be methyl. In some embodiments, one R' can be hydrogen and one R' can be methyl. In some embodiments, at least one R' can be ethyl. In some embodiments, both R' can be ethyl. In some embodiments, one R' can be hydrogen and one R' can be ethyl. In some embodiments, one R' can be methyl and one R' can be ethyl.

R can be selected from C$_{1-8}$ alkyl, C$_{1-8}$ heteroalkyl having 1-4 heteroatoms independently selected from N, O, and S, C$_{3-6}$ cycloalkyl, 3-10 membered heterocycloalkyl having 1-4 heteroatoms independently selected from N, O, and S, C$_{6-10}$ aryl, and 5-10 membered heteroaryl having 1-4 heteroatoms independently selected from N, O, and S. In some embodiments, at least one R can be C$_{1-8}$ alkyl. In some embodiments, both R can be C$_{1-8}$ alkyl. In embodiments, R is selected from methyl, ethyl, propyl, butyl, pentyl, or hexyl. In embodiments, at least one R can be ethyl. In embodiments, both R can be ethyl. In embodiments, at least one R can be heteroalkyl. In refinements of the foregoing embodiment, the at least one R can be C$_{1-8}$ heteroalkyl having 1 to 4 heteroatoms selected from N, O, and S. In embodiments, both R can be heteroalkyl. In refinements of the foregoing embodiment, each R can independently be C$_{1-8}$ heteroalkyl having 1 to 4 heteroatoms selected from N, O, and S. In embodiments, one or both R can be selected from methoxy, ethoxy, propoxy, and butoxy. In embodiments, at least one R can be C$_{3-6}$ cycloalkyl. In embodiments, each R can be C$_{3-6}$ cycloalkyl. In embodiments, at least one R can be a 3 to 10 member heterocycle having 1 to 4 heteroatoms selected from N, O, and S. In embodiments, both R can be a 3 to 10 member heterocycle having 1 to 4 heteroatoms selected from N, O, and S. In some embodiments, at least one R can be C$_{6-10}$ aryl. In some embodiments, both R can be C$_{6-10}$ aryl. In some embodiments, at least one R can be phenyl. In some embodiments, both R can be phenyl. In embodiments, at least one R can be a 5 to 10 membered heteroaryl having 1 to 4 heteroatoms independently selected from N, O, and S. In embodiments, both R can be 5 to 10 membered heteroaryl having 1 to 4 heteroatoms independently selected from N, O, and S. In some embodiments, one R can be alkyl and one R can be heteroalkyl. In some embodiments, one R can be alkyl and one R can by cycloalkyl. In some embodiments, one R can be alkyl and one R can be heterocycloalkyl. In some embodiments, one R can be alkyl and one R can be aryl. In some embodiments, one R can be alkyl and one R can be heteroaryl. In some embodiments, one R can be heteroalkyl and one R can by cycloalkyl. In some embodiments, one R can be heteroalkyl and one R can be heterocycloalkyl. In some embodiments, one R can be heteroalkyl and one R can be aryl. In some embodiments, one R can be heteroalkyl and one R can be heteroaryl. In some embodiments, one R can be cycloalkyl and one R can be heterocycloalkyl. In some embodiments, one R can be cycloalkyl and one R can be aryl. In some embodiments, one R can be cycloalkyl and one R can be heteroaryl. In some embodiments, one R can be heterocycloalkyl and one R can be aryl. In some embodiments, one R can be heterocycloalkyl and one R can be heteroaryl. In some embodiments, one R can be aryl and one R can be heteroaryl.

In embodiments, the compound of formula (I) can have a structure selected from the arum consisting of:

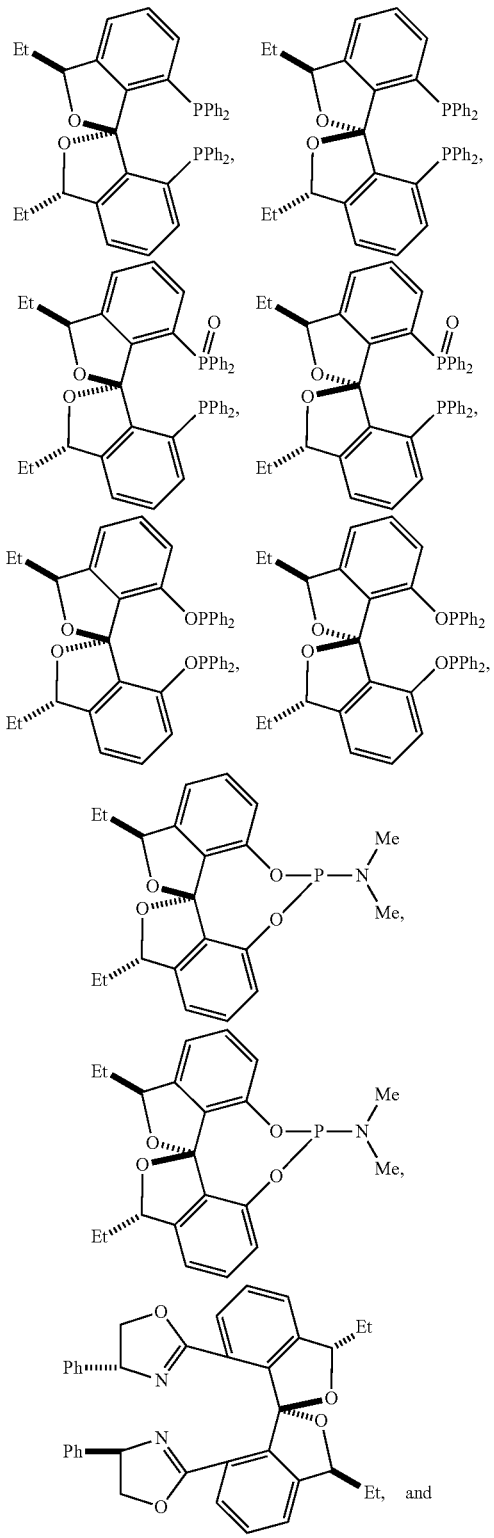

-continued

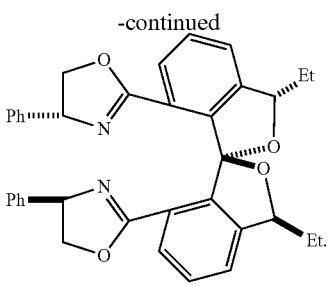

Another aspect of the disclosure provides a catalyst including a compound of the disclosure and a transition metal. The catalysts of the disclosure can advantageously be used to bring about one or more transformations, including, but not limited to, asymmetric hydroarylation, asymmetric allylic alkylation, hydrogenation, and asymmetric intermolecular Heck reaction and domino cyclization.

The transition metal of the catalyst can comprise iridium, palladium, rhodium, platinum, copper, nickel, cobalt, or gold. In some embodiments, the transition metal can be iridium. In some embodiments, the transition metal can be palladium.

The disclosure further provides methods of preparing a catalyst, the method including admixing a compound of formula (I) and a transition metal to form the catalyst. In embodiments, the transition metal is provided in a salt form. In embodiments, the transition metal or salt thereof comprises bis(1,5-cyclooctadiene)diiridium(I) dichloride ([Ir(COD)Cl]$_2$), allylpalladium(II) chloride dimer ([Pd(allyl)Cl]$_2$), or bis(dibenxylideneacetone)palladium(0) (Pd(dba)$_2$).

The compound of formula (I) and the transition metal can be admixed under any suitable conditions for forming the catalyst. The compound of formula (I) and the transition metal can be provided in a molar ratio of about 6:1 to about 1:1, about 5:1 to about 1:1, about 4:1 to about 1:1, about 3:1 to about 1:1, about 2.5:1 to about 1:1, about 2:1 to about 1:1, about 1.5:1 to about 1:1, about 1.25:1 to about 1:1. In embodiments, the compound of formula (I) is provided in a molar excess relative to the amount of transition metal.

Another aspect of the disclosure provides methods of forming a reaction product having a chiral center, the methods comprising admixing a first reactant, a second reactant, and the catalyst of the disclosure under conditions sufficient to allow reaction of the first reactant and the second reactant to form the reaction product, wherein the reaction product comprises a chiral center and is produced in an enantiomeric excess (ee) (e.g., is not racemic).

In embodiments, the reaction product is the product of an asymmetric hydroarylation. The first reactant and second reactant can be an asymmetric alkene and an aromatic compound. An asymmetric alkene is an alkene wherein each carbon of the double bond comprises different substituents from the other carbon of the double bond. For example, one carbon of the double bond can comprise two methyl group substituents, while the other carbon of the double bond comprises a methyl and a hydrogen. Sufficient conditions for asymmetric hydroarylation are well known in the art.

In embodiments, the reaction product is the product of an asymmetric allylic alkylation. The first reactant and second reactant can be an asymmetric alkene having a leaving group in an allylic position and a nucleophilic compound. Sufficient conditions for an asymmetric allylic alkylation are well known in the art.

In embodiments, the reaction product is the product of an asymmetric intermolecular Heck reaction. The first reactant and second reactant can be an unsaturated halide (e.g., vinyl halide or aryl halide) or unsaturated triflate (e.g., vinyl triflate or aryl triflate) and an alkene. Sufficient conditions for a Heck reaction are well known in the art.

In embodiments, the reaction product is the product of a hydrogenation reaction. The first reactant and second reactant can include hydrogen gas and an unsaturated compound (e.g., alkene or alkyne). Sufficient conditions for hydrogenation are well known in the art.

The compounds disclosed herein may be identified either by their chemical structure and/or chemical name herein. When the chemical structure and chemical name conflict, the chemical structure is determinative of the identity of the compound.

Unless otherwise indicated, terms and abbreviations used in this specification include the normal and customary meaning to those in the relevant field.

As the present disclosure's contribution is not limited to particular embodiments or aspects disclosed herein, the disclosure provides to one of ordinary skill in the art additional embodiments including changes and modifications to adapt to various usages and conditions. For example, changes and modifications to materials, methods of synthesis, or procedures described herein will be apparent to one of ordinary skill.

When ranges are used herein for physical properties, such as molecular weight, or chemical properties, such as chemical formulae, all combinations and subcombinations of ranges and specific embodiments therein are intended to be included.

Chemical Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-7}$alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "heteroalkyl" is defined similarly as alkyl, except the chain further contains one to four heteroatoms independently selected from oxygen, nitrogen, and sulfur. Nonlimiting examples of heteroalkyl groups include methoxy (O-methyl), ethoxy (—O-ethyl), propoxy (—O-propyl), and butoxy (O-n-butyl, O-sec-butyl, or O-t-butyl). The heteroatom(s) can be the point of attachment to the rest of the compound (e.g., —OCH$_3$) or can be within the alkyl chain (e.g., —CH$_2$OCH$_2$CH$_3$ and —CH$_2$CH$_2$NHCH$_3$).

As used herein, the term "cycloalkyl" refers to an aliphatic cyclic hydrocarbon group containing three to six carbon atoms (e.g., 3, 4, 5, or 6 carbon atoms). The term $C_n$ means the cycloalkyl group has "n" carbon atoms. For example, $C_5$ cycloalkyl refers to a cycloalkyl group that has 5 carbon atoms in the ring. $C_{3-6}$ cycloalkyl refers to cycloalkyl groups having a number of carbon atoms encompassing the entire range (i.e., 3 to 6 carbon atoms), as well as all subgroups (e.g., 3-4, 3-5, 4-6, 4-5, 3, 4, 5, and 6 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

As used herein, the term "heterocycloalkyl" is defined similarly as cycloalkyl, except the ring contains one to four heteroatoms independently selected from oxygen, nitrogen, and sulfur. Nonlimiting examples of heterocycloalkyl groups include piperdine, tetrahydrofuran, tetrahydropyran, dihydrofuran, morpholine, oxazepaneyl, and the like. Cycloalkyl and heterocycloalkyl groups can be saturated or partially unsaturated ring systems optionally substituted with, for example, one to three groups, independently selected from alkyl, alkylene, OH, C(O)NH$_2$, NH$_2$, oxo (═O), aryl, haloalkyl, halo, and OH. Heterocycloalkyl groups optionally can be further N-substituted as described herein. Unless otherwise indicated, a heterocycloalkyl group can be an unsubstituted heterocycloalkyl group or a substituted heterocycloalkyl group.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, fluorenyl, tetralinyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to four ring atoms are selected from oxygen, nitrogen, and sulfur, and the remaining ring atoms are carbon, said ring system being joined to the remainder of the molecule by any of the ring atoms. Nonlimiting examples of heteroaryl groups include, but are not limited to, pyridyl, pyridazinyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, thienyl, quinolinyl, isoquinolinyl, benzoxazolyl, benzimidazolyl, benzofuranyl, benzothiazolyl, triazinyl, triazolyl, purinyl, pyrazinyl, purinyl, indolinyl, phthalzinyl, indazolyl, quinolinyl, isoquinolinyl, cinnolinyl, quinazolinyl, naphthyridinyl, pyridopyridinyl, indolyl, 3H-indolyl, pteridinyl, and quinooxalinyl. Unless otherwise indicated, a heteroaryl group can be an unsubstituted heteroaryl group or a substituted heteroaryl group.

As used herein, a protecting group is a readily removable group that is not a constituent of the particularly desired end product of the compounds of the present invention. Protecting groups can be removed readily (i.e., without the occurrence of undesired secondary reactions) for example by solvolysis, reduction, or photolysis. Non-limiting examples of protecting groups include, but are not limited to, methoxymethyl acetal (MOM), benzyl (Bn), and benzyloxymethyl acetal (BOM) groups.

A "substituted" functional group (e.g., a substituted alkyl, heteroalkyl, cycloalkyl, heterocycloalkyl, aryl, or heteroaryl) is a functional group having at least one hydrogen radical that is substituted with a non-hydrogen radical (i.e., a substituent). Examples of non-hydrogen radicals (or substituents) include, but are not limited to, alkyl, cycloalkyl, alkenyl, cycloalkenyl, alkynyl, ether, aryl, heteroaryl, heterocycloalkyl, hydroxyl, oxy (or oxo), alkoxy, ester, thioester, acyl, carboxyl, cyano, nitro, amino, sulfhydryl, and halo. When a substituted alkyl group includes more than one non-hydrogen radical, the substituents can be bound to the same carbon or two or more different carbon atoms.

As used herein, the term "enantiomeric excess" refers to an excess of one enantiomer of a chiral compound relative to the amount of the other enantiomer present in a composition, for example, about a 5%, about a 10%, about a 25%, about a 50%, about a 75%, about an 85%, about a 90%, or about a 95% excess of one enantiomer relative to the other. A racemic mixture has an ee of 0%, while a single completely pure enantiomer has an ee of 100%.

Preparation of SPIROL and SPIROL-Based Ligands

Another aspect of the disclosure provides preparing compound (S,S,S)-4:

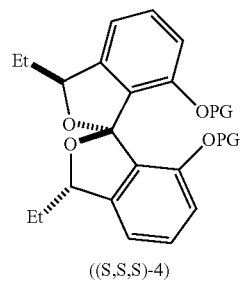

((S,S,S)-4)

the method comprising (a) cooling a solution of compound (S)-2:

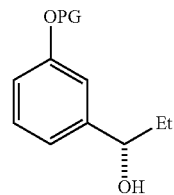

to 0° C., wherein PG is a hydroxy protecting group, (b) adding an organolithium reagent to the cooled solution of step (a) to form a mixture, (c) warming the mixture of step (b) to room temperature and keeping it at room temperature to dissolve suspended material and form a solution, (d) cooling the solution of step (c) to 0° C., (e) admixing the solution of step (d) and diethyl carbonate at 0° C. (f) warming the reaction mixture of step (e) to room temperature, and (g) admixing the reaction mixture of step (f) with acetic acid.

In embodiments of step (a), the protecting group can be selected from the group consisting of methoxymethyl acetal (MOM), benzyl (Bn), and benzoxymethyl acetal (BOM). The solution of compound (S)-2 can be cooled to 0° C. using any suitable means, for example, an ice bath. The rate of cooling the solution of compound (S)-2 is not particularly limiting as long as the solution is at 0° C. when the organolithium reagent is added in step (b). The solvent of the solution of compound (S)-2 can be any suitable solvent that solvates the compound of (S)-2. In general, the solvent of the solution of compound (S)-2 will be a non-aqueous, dry solvent such that there is no water present for the organolithium reagent added in step (b) to react with. Suitable solvents can include, but are not limited to, hexanes, toluene, pentane, tetrahydrofuran, diethyl ether, hexamethylphosphoramide (HMPA), and combinations of the foregoing. The solvent can also be selected to moderate the rate of metalation of compound (S)-2 by the organolithium reagent, as is known in the art.

In embodiments of step (b), the organolithium reagent can be any organolithium reagent capable of lithiating compound (S)-2 at the carbon between the protected hydroxyl group and the propanol substituent. Suitable organolithium reagents include, but are not limited to, n-butyllithium, t-butyllithium, s-butyllithium, isopropyllithium, methyllithium, and pentyllithium. In embodiments, the organolithium reagent comprises n-butyllithium, t-butyllithium, or s-butyllithium. In embodiments, the organolithium reagent comprises n-butyllithium. The organolithium reagent can be added to the solution of step (a) in a molar ratio of about 2:1 to about 1:1 relative to the amount of compound (S)-2. The organolithium reagent can be added over any suitable amount of time, for example, over three hours, over two hours, or over one hour.

In embodiments of step (c), warming to room temperature takes place without the addition of heat, for example, the cold bath is removed and the mixture allowed to warm to room temperature, unassisted, over time. The mixture can be allowed to warm to room temperature for at least 12 hours, at least 10 hours, at least 8 hours, at least 6 hours, at least 4 hours, at least 3 hours, at least 2 hours, or at least 1 hour. In embodiments, step (c) further comprises adding additional solvent to dissolve the suspended material. In embodiments, the additional solvent comprises tetrahydrofuran.

In embodiments of step (d), the solution of step (c) can be cooled to 0° C. using any suitable means, for example, an ice bath. The rate of cooling the solution of step (c) is not particularly limiting as long as the solution is at 0° C. when the diethyl carbonate is added in step (e).

In embodiments of step (e), the solution of step (d) can be mixed with diethyl carbonate. The molar ratio of diethyl carbonate added relative to the amount of compound (S)-2 used can be in a range of about 2:1 to about 1:1. In some embodiments, the moles of diethyl carbonate added is about half the moles of compound (S)-2 used, plus an excess of 5 to 10%, resulting in a molar ratio of diethyl carbonate to compound (S)-2 of about 1.8:1 to about 1.9:1. The mixture of diethyl carbonate with the solution of step (d) can be stirred for any amount of time suitable to allow complete reaction, for example, about 1 hour, about 2 hours, about 3 hours, about 4 hours, or about 5 hours.

In embodiments of step (f), warming to room temperature takes place without the addition of heat, for example, the cold bath is removed and the mixture allowed to warm to room temperature, unassisted, over time. The mixture can be allowed to warm to room temperature for at least 12 hours, at least 10 hours, at least 8 hours, at least 6 hours, at least 4 hours, at least 3 hours, at least 2 hours, or at least 1 hour.

In embodiments of step (g), the mixture of step (f) can be admixed with excess acetic acid. The acetic acid can be added at ambient temperature (e.g., 20° C. to 25° C.). The acetic acid can be added slowly, for example, over 5 minutes, over 10 minutes, over 30 minutes, or over an hour or more. The resulting mixture can be stirred for any amount of time suitable to allow complete reaction, for example, about 1 hour, about 2 hours, about 3 hours, about 4 hours, or about 5 hours.

In embodiments, the method further comprises quenching the reaction mixture of step (e) with a saturated solution of sodium bicarbonate (NaHCO$_3$). The method can further comprise separating the aqueous fraction and extracting with ethyl acetate (EtOAc) at least three times. The combined organic layers can be washed with brine, dried over sodium sulfate (Na$_2$SO$_4$) and concentrated in vacuo, and purified by flash column chromatography (FCC) (SiO$_2$ 10% EtOAc in hexanes).

Scheme 1:

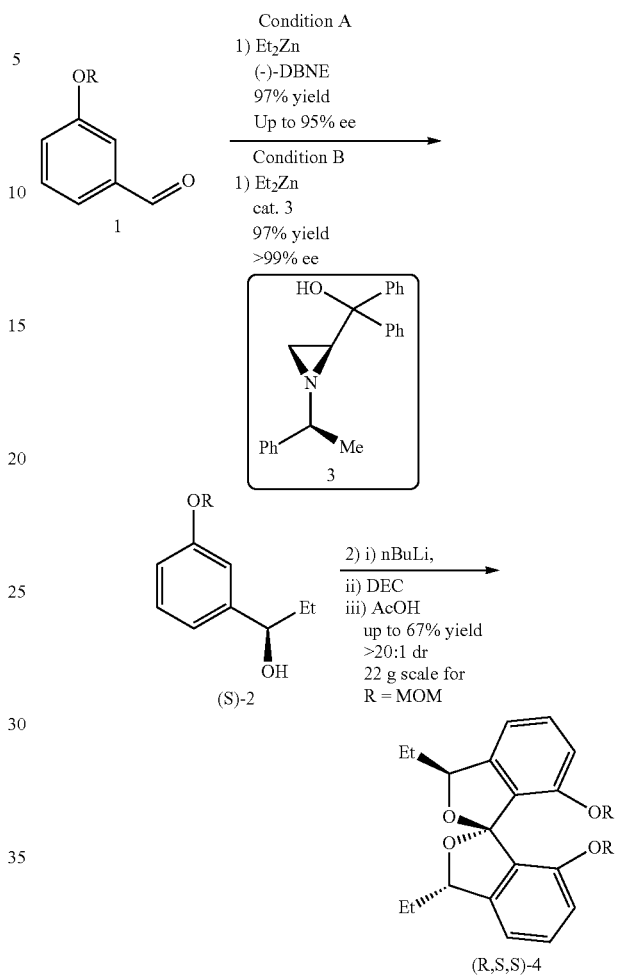

R = MOM, Bn and BOM

The spirocyclic core (4) is promptly assembled in two steps from simple benzaldehydes 1. Succinctly, this is achieved by an enantioselective dialkylzinc addition followed by a one-pot deprotonation/dimerization/spirocyclization cascade (Scheme 1). In addition to methoxymethyl acetal (MOM)-protected 2 and 4, the same transformations have been applied to generate benzyl (Bn)- and benzyloxymethyl acetal (BOM)-protected variants 2 and 4 with similar yields and selectivities. The Bn-protected route is favored because the benzylated analog of 1 is commercially available (shortening the route) and its later deprotection is achieved cleanly. Using asymmetric Noyori alkylzinc addition (one of the most reliable and well-understood enantioselective transformations) allows avoiding the racemate resolution steps that are used in SPINOL construction. The spirocyclic core constructed one-pot dimerization of 2 into 4 also offers synthetic advantage as SPINOL-core construction requires significantly more steps/reagents/waste. Finally, the spiroketalization method is truly robust, offering 67% yield of cyclized product, 15% of recovered starting material, and 9% of intermediate isobenzofuranone 5.

The deprotection of 4 (R=Bn, BOM) can be carried out quantitatively under standard hydrogenolysis conditions. The resulting diol (R,S,S)-6 can be equilibrated cleanly and with moderate selectivities to the epimer (S,S,S)-6 by stirring with silica. The diol mixture can be almost quantitatively converted to the ditriflates 7 with unchanged diastereomeric ratio (d.r.) under standard triflation conditions (Scheme 2).

Scheme 2:

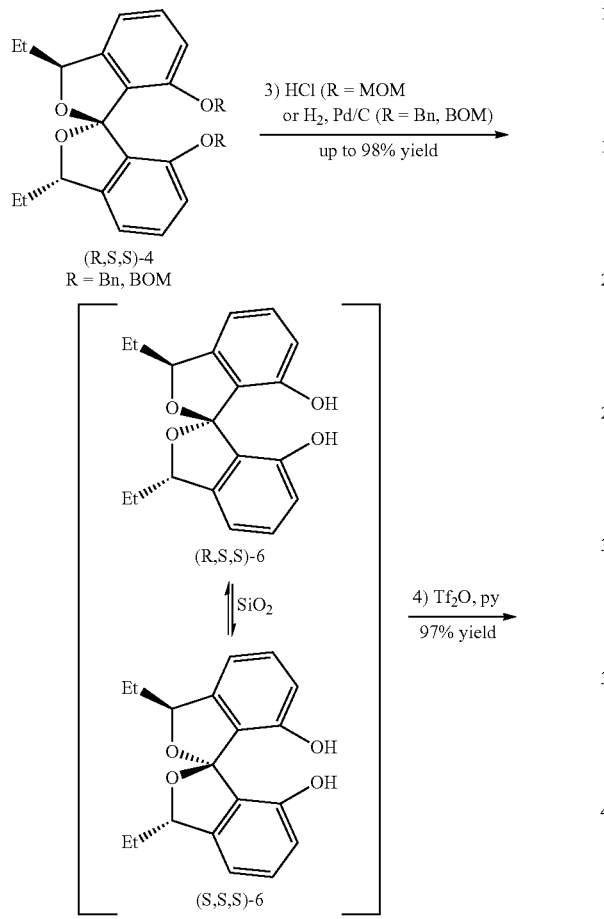

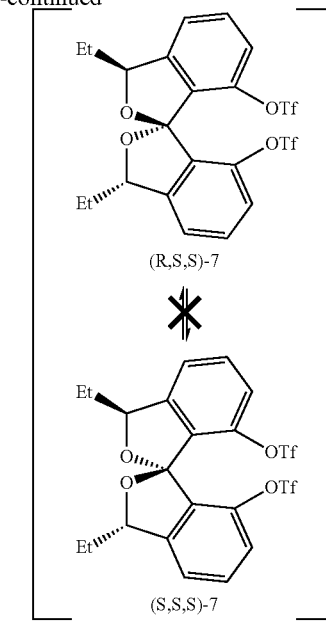

Although the diastereomers of 7 do not interconvert and can be separated by flash column chromatography on silica, a chemical resolution was found to be more convenient on a larger scale (Scheme 3). A palladium-catalyzed coupling to diphenylphosphine oxide at 80° C. selectively reacts with (S,S,S)-7 to afford phosphine oxide (S,S,S)-8 in excellent yield, while ditriflate (R,S,S)-7 is recovered quantitatively. Phosphine oxide (S,S,S)-8 can then be elaborated to phosphine oxide/phosphine (S,S,S)-SPIRAP(O) 10 or diphosphine (S,S,S)-SPIRAP 11. The key in this route is recrystallization of (S,S,S)-8 in cyclohexane to further increase its enantiopurity that allows to generate highly pure ligands (S,S,S)-10 and (S,S,S)-11. Conditions for the direct formation of (S,S,S)-11 from (S,S,S)-9 were found which maintain an excellent yielding route. It should be noted that the sequence going from (S,S,S)-8 to (S,S,S)-11 is one step shorter than the reported sequence for the actual spiro diphosphine (SDP) ligands as the introduction of the second phosphine functionality is done in a single step (vs. a known 2-step protocol).

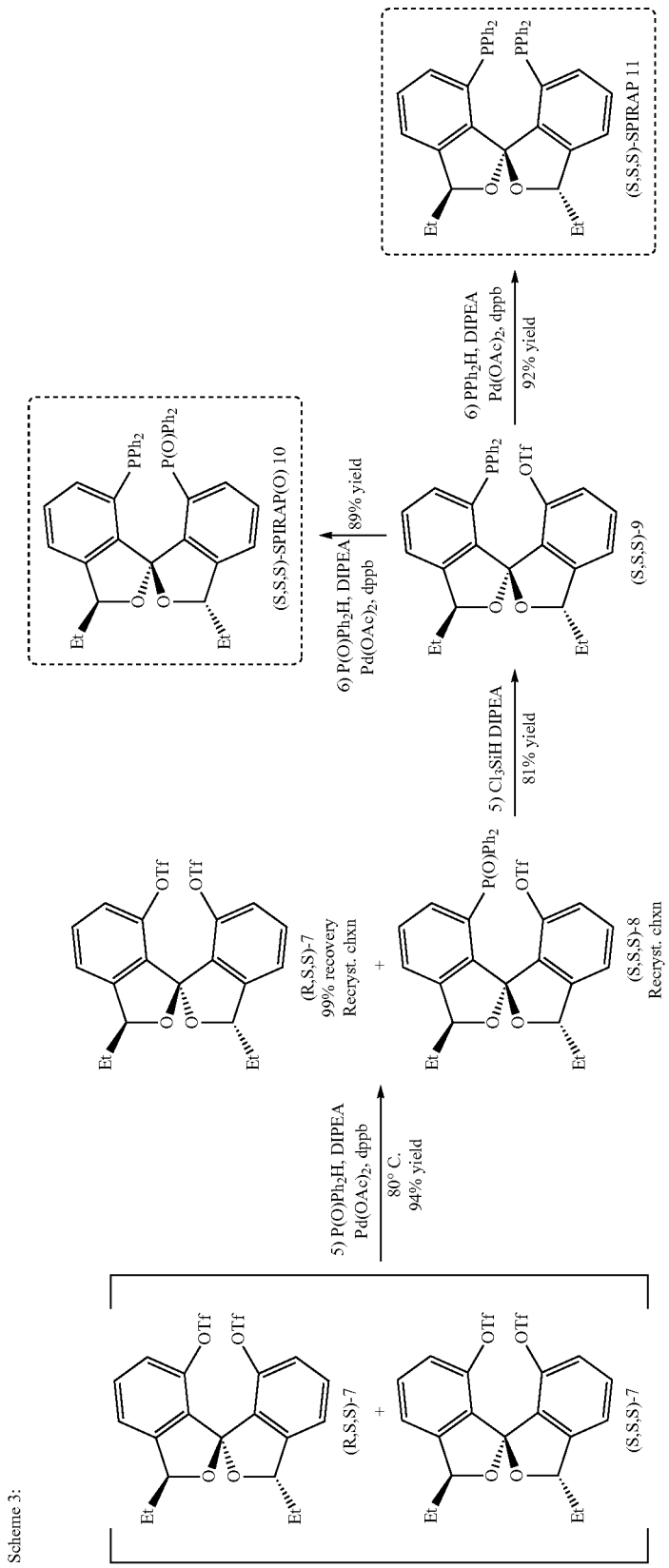

In addition, the recovered ditriflate (R,S,S)-7 could be purified by recrystallization in cyclohexane, and then coupled to diphenyl phosphine oxide under similar conditions but at 100° C. to afford (R,S,S)-8 in good yield. This compound could then be elaborated in a similar fashion to phosphine oxide/phosphine (R,S,S)-10 and diphosphine (R,S,S)-11 in good yields (Scheme 4).

Scheme 4:

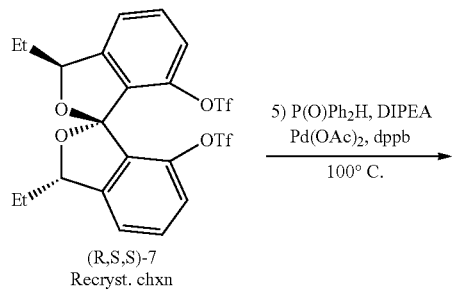

(R,S,S)-7
Recryst. chxn

5) P(O)Ph₂H, DIPEA
Pd(OAc)₂, dppb
100° C.

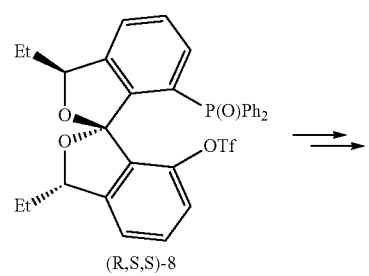

(R,S,S)-8

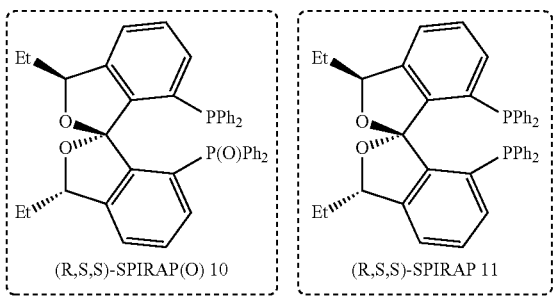

(R,S,S)-SPIRAP(O) 10     (R,S,S)-SPIRAP 11

Another aspect of the disclosure provides a method of preparing compound (S,S,S)-8:

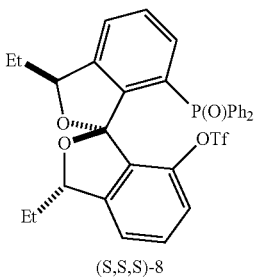

(S,S,S)-8 the method comprising admixing diphenylphosphine oxide with a triflate compound comprising (S,S,S)-7

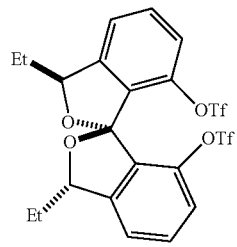

and, optionally, compound (S,R,S)-7

, in the presence of a catalyst to form compound (S,S,S)-8, wherein the temperature of the admixing is 70° C. to 90° C.

In embodiments, the triflate compound further comprises (R,S,S)-7.

The diphenylphosphine oxide and the triflate compound can be admixed in an oxygen-free atmosphere, for example, in a glove box. The diphenylphosphine oxide and triflate compound can be admixed in a molar ratio of about 1:1. In embodiments, the diphenylphosphine oxide can be added in a slight molar excess, relative to the triflate compound. The catalyst can be a palladium (II) complex, a platinum (II) complex, a Palladium (0) complex, or a platinum (0) complex. In embodiments, the catalyst comprises palladium (II) acetate, bis(dibenzylideneacetone)palladium(0), or tris(dibenzylideneacetone)dipalladium(0). In embodiments, the catalyst comprises palladium (II) acetate. In embodiments, the admixing comprises mixing the diphenylphosphine oxide and triflate compound in a solvent. Suitable solvents include, but are not limited to, dimethyl sulfoxide (DMSO) and N,N-diisopropylethylamine. The admixing can be done at ambient temperature (20° C. to 25° C.). The reaction mixture can be stirred at ambient temperature for at least 15 minutes, at least 30 minutes, at least an hour, or at least 2 hours. The reaction mixture can then be heated to at least 60° C., at least 70° C., at least 80° C., or at least 90° C., for example, in a range of about 70° C. to about 90° C., and the mixture can stir at elevated temperature for at least 4 hours, at least 6 hours, at least 8 hours, at least 10 hours, or at least 12 hours. The reaction mixture can then be cooled to room temperature and (S,S,S)-8 isolated by partitioning between EtOAc and NaHCO₃, extraction of the aqueous phase with EtOAc, and washing, drying, and concentrating the combined organic layers.

Another aspect of the disclosure provides a method of preparing compound (R,S,S)-8:

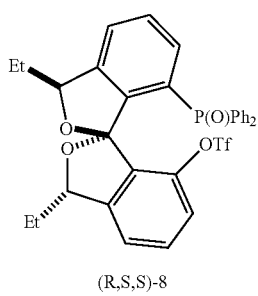

(R,S,S)-8 the method comprising admixing diphenylphosphine oxide with triflate compound

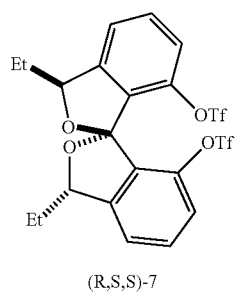

(R,S,S)-7 in the presence of a catalyst to form compound (R,S,S)-8 wherein the temperature of the admixing is 90° C. to 110° C.

The diphenylphosphine oxide and the triflate compound can be admixed in an oxygen-free atmosphere, for example, in a glove box. The diphenylphosphine oxide and triflate compound can be admixed in a molar ratio of about 1:1. In embodiments, the diphenylphosphine oxide can be added in a slight molar excess, relative to the triflate compound. The catalyst can be a palladium (II) complex, a platinum (II) complex, a Palladium (0) complex, or a platinum (0) complex. In embodiments, the catalyst comprises palladium (II) acetate, bis(dibenzylideneacetone)palladium(0), or tris(dibenzylideneacetone)dipalladium(0). In embodiments, the catalyst comprises palladium (II) acetate. In embodiments, the admixing comprises mixing the diphenylphosphine oxide and triflate compound in a solvent. Suitable solvents include, but are not limited to, dimethyl sulfoxide (DMSO) and N,N-diisopropylethylamine. The admixing can be done at ambient temperature (20° C. to 25° C.). The reaction mixture can be stirred at ambient temperature for at least 15 minutes, at least 30 minutes, at least an hour, or at least 2 hours. The reaction mixture can then be heated to at least 80° C., at least 90° C., at least 100° C., or at least 110° C., for example, in a range of about 90° C. to about 110° C., and the mixture can stir at elevated temperature for at least 4 hours, at least 6 hours, at least 8 hours, at least 10 hours, or at least 12 hours. The reaction mixture can then be cooled to room temperature and (S,S,S)-8 isolated by partitioning between EtOAc and NaHCO$_3$, extraction of the aqueous phase with EtOAc, and washing, drying, and concentrating the combined organic layers.

It must be emphasized that the preparation of diphosphine ligands (R,S,S)-SPIRAP and (S,S,S)-SPIRAP is significantly shorter than for the construction of the corresponding SPINOL-based ligands. Altogether, the conciseness and robustness of this sequence allows achieving a faster, more efficient, and economical assembly of SPIROL-based ligands in comparison with the SPINOL-based ligands such as SDP.

Another advantage the preparation of SPIROL derivatives is that it is highly modular. The exceptionally direct route to the diol core 6 can be used to obtain, for example, useful diphosphinites (R,S,S)-12 and (S,S,S)-12 (easily separated by flash column chromatography on silica) and phosphoramidites (R,S,S)-13 and (S,S,S)-13 in only a total of 4 steps (Scheme 5).

Scheme 5:

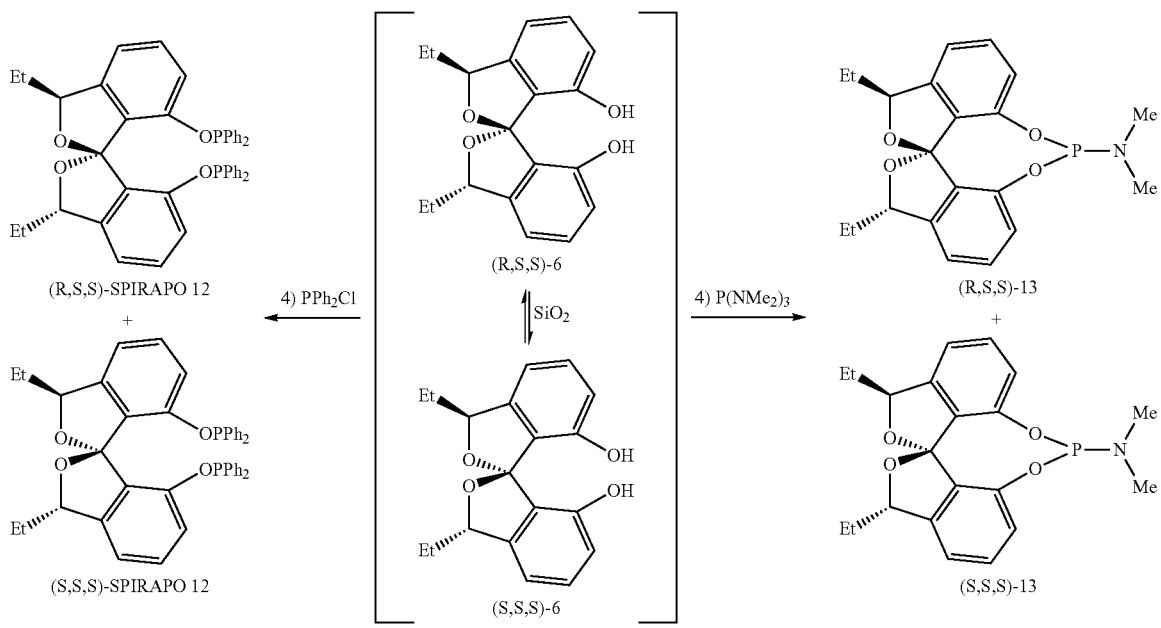

Figure 2A:
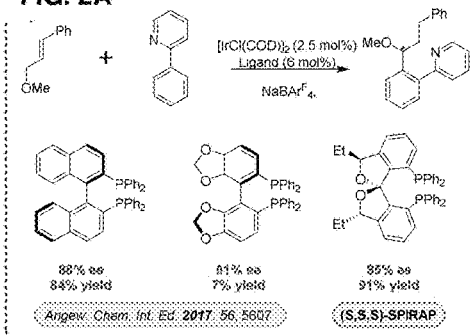
FIG. 2A shows the use of Ir(I) complexed with (S,S,S)-SPIRAP 11 for the hydroarylation of olefins.
Figure 2B:
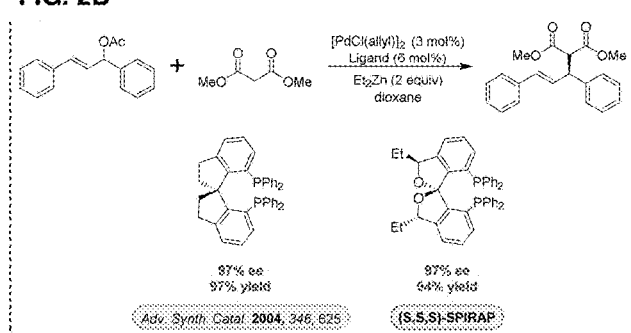
FIG. 2B shows the direct comparison of (S,S,S)-SPIRAP 11 and commercially available spiro diphosphine (SDP) ligand in Pd(0)-catalyzed allylic alcohol substitution with malonates.
Figure 2C:
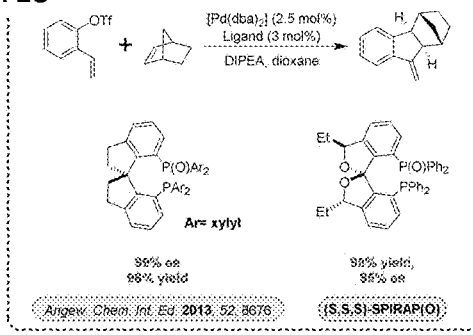
FIG. 2C shows the use of (S,S,S)-10 ligand in asymmetric Pd(0)-catalyzed Heck reactions.
Figure 2D:
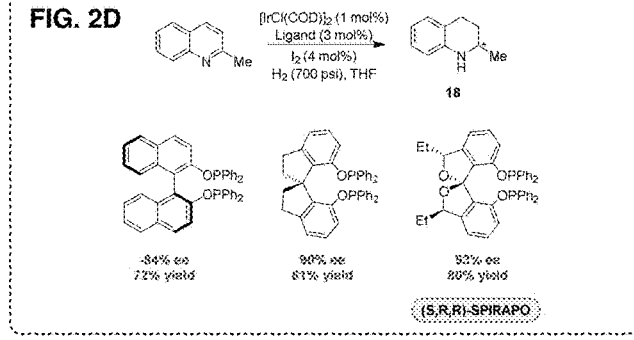
FIG. 2D shows the use of (S,R,R)-12 ligand in asymmetric Ir(I)-catalyzed hydrogenation reactions.
Figure 3A:
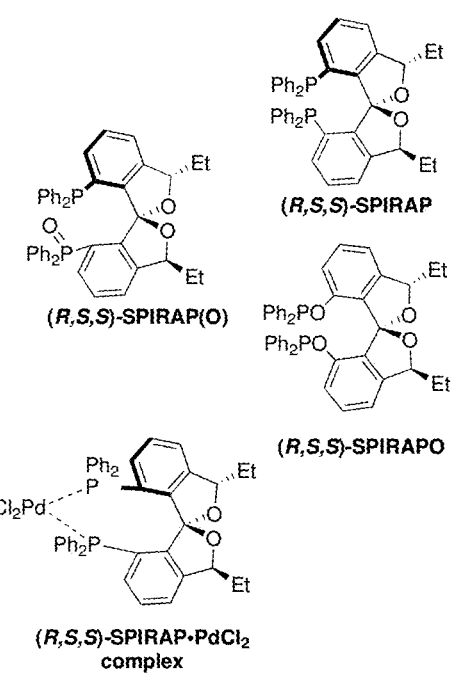
FIG. 3A shows (R,S,S)/(S,R,R) diastereomers of SPIRAP, SPIRAP(O), SPIRAPO, and SPIRAP-PdCl$_2$ complexes of the disclosure.
Figure 3B:
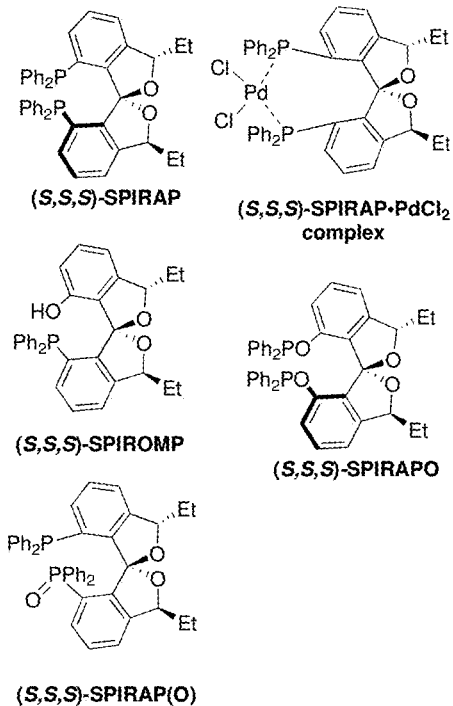
FIG. 3B shows (R,R,R)/(S,S,S) diastereomers of, SPIRAP(O), SPIRAPO, and SPIRAP-PdCl$_2$ complexes of the disclosure.
Figure 4A:
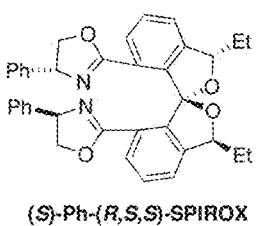
FIG. 4A shows (S)-Ph-(R,S,S)-SPIROX of the disclosure.
Figure 4B:
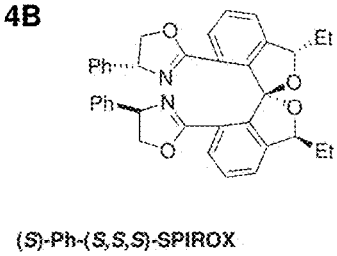
FIG. 4B shows (S)-Ph-(S,S,S)-SPIROX of the disclosure.

The performance of some of the ligands produced were tested in a number of unrelated transformations (FIG. 2). FIG. 2A outlines the use of Ir(I) complexed with (S,S,S)-SPIRAP 11 for the hydroarylation of olefins that appeared in literature this year. For this specific reaction, ligand (S,S,S)-11 demonstrated the best performance, surpassing BINAP and modified BINAP ligands. The direct comparison of ligand (S,S,S)-SPIRAP 11 and commercially available SDP ligand (FIG. 2B) in Pd(0)-catalyzed allylic alcohol substitution with malonates indicates that both ligands perform similarly well in this reaction. In line with these observations were the results obtained for phosphine oxide/phosphine (S,S,S)-10 and diphosphinite (S,R,R)-12 in asymmetric Pd(0)-catalyzed Heck reactions (FIG. 2C) and asymmetric Ir(I)-catalyzed hydrogenation reaction (FIG. 2D), respectively.

The SPIROL-based ligands such as (S,S,S)-10, (S,S,S)-11, and (S,R,R)-12 demonstrate very similar performance when compared side-by-side to commercially available SPINOL-based ligands. Concise and fast assembly of these ligands without chiral resolution of racemic intermediate makes this class of ligands significantly cheaper and more available than SPINOL-based ligands.

EXAMPLES

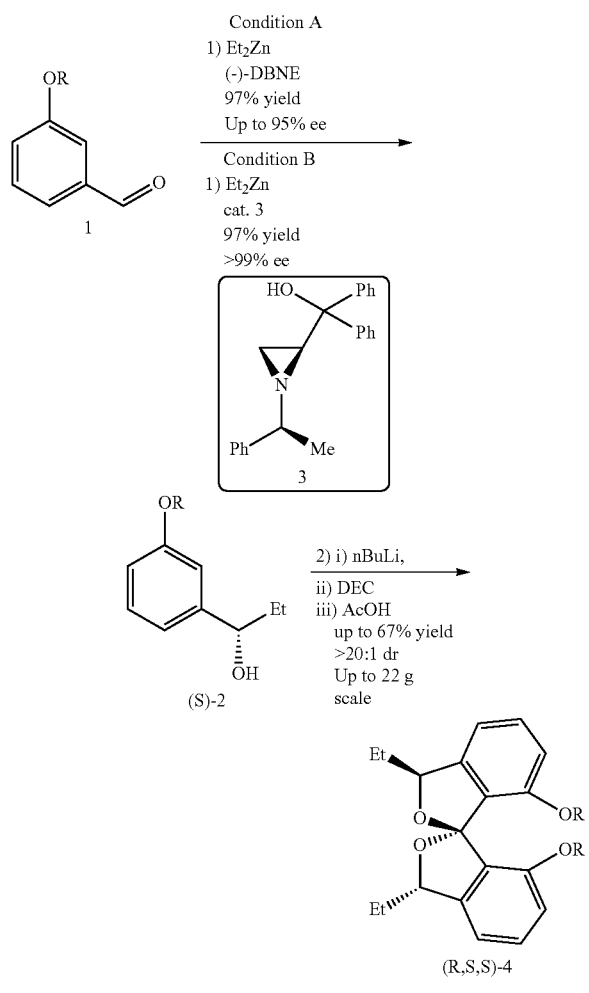

3-(methoxymethyl)benzaldehyde (1,R=MOM)

3-hydroxybenzaldehyde (24.0 g, 196.5 mmol), dichloromethane (DCM) (500 mL), and N,N-Diisopropylethylamine (100 mL, 589.6 mmol) were cooled to 0° C. before adding chloromethyl methyl ether (23 mL, 303.6 mmol) over 2 hours with a venting needle to handle the fumes. Reaction mixture was then warmed to room temperature. After 17 h at room temperature, reaction mixture was quenched with a saturated aqueous solution of $NaHCO_3$ (500 mL). After separating the phases the aqueous layer was extracted with DCM twice. Combined organic layers were washed with brine, dried over $Na_2SO_4$, and concentrated in vacuo. Crude product was purified by FCC ($SiO_2$, 20% EtOAc in hexanes) to obtain the desired product as pale yellow liquid (31.94 g, 97.8% yield). $^1$H NMR (700 MHz, Chloroform-d) δ 9.98 (s, 1H), 7.57-7.51 (m, 2H), 7.46 (t, J=7.8 Hz, 1H), 7.32-7.28 (m, 1H), 5.24 (s, 2H), 3.49 (s, 3H). $^{13}$C NMR (176 MHz, cdcl$_3$) δ 191.96, 157.76, 137.82, 130.11, 123.81, 122.83, 115.93, 94.39, 56.16.

3-((benzyloxy)methoxy)benzaldehyde (1R=BOM)

BOM-protected benzaldehyde was obtained following Dubinnyi, et al., Chem.—A Eur. J. 2014, 21 (10), 3942-3947.

3-(benzyloxymethyl)benzaldehyde (1,R=Bn)

3-hydroxybenzaldehyde (24.0 g, 196.5 mmol), DCM (500 mL), and N,N-Diisopropylethylamine (100 mL, 589.6 mmol) were cooled to 0° C. before adding chloromethyl methyl ether (23 mL, 303.6 mmol) over 2 hours with a venting needle to handle the fumes. Reaction mixture was then warmed to room temperature. After 17 h at room temperature, reaction mixture was quenched with a saturated aqueous solution of $NaHCO_3$ (500 mL). After separating the phases the aqueous layer was extracted with DCM twice. Combined organic layers were washed with brine, dried over $Na_2SO_4$, and concentrated in vacuo. Crude product was purified by FCC ($SiO_2$, 20% EtOAc in hexanes) to obtain the desired product as pale yellow liquid (31.94 g, 97.8% yield).

(S)-1-(3-(methoxymethyl)phenyl)propan-1-ol (2,R=MOM)

a) Using N,N-Dibutyl-D-(−)-norephedrine ((−)-DBNE)
Aldehyde 1 (31.92 g, 192.1 mmol), hexanes (370 mL), and N,N-Dibutyl-D-(−)-norephedrine (3.8 mL, 13.6 mmol) were cooled to 0° C. before adding a 1 M solution of diethylzinc in hexanes (430 mL, 430 mmol) portionwise over 2 hours. After 27 h at 0° C., reaction mixture was quenched with an aqueous solution of HCl 1 M (150 mL) and then filtered with DCM washings. Water (400 mL) was added to the filtrate. After separating the layers, the aqueous fraction was extracted with DCM twice. Combined organic layers were washed with brine, dried over $Na_2SO_4$, and concentrated in vacuo. Crude product was purified by FCC ($SiO_2$, 30% EtOAc in hexanes) to obtain (S)-2 (R=MOM) as pale yellow oil (36.5 g, 96.8% yield). $^1$H NMR (700 MHz, Chloroform-d) δ 7.29-7.24 (m, 1H), 7.03 (t, J=2.0 Hz, 1H), 6.99 (dt, J=7.4, 1.2 Hz, 1H), 6.96 (ddd, J=8.2, 2.6, 1.0 Hz, 1H), 5.19 (s, 2H), 4.60-4.55 (m, 1H), 3.49 (s, 3H), 1.85-1.71 (m, 2H), 0.94 (t, J=7.4 Hz, 3H). $^{13}$C NMR (176 MHz, cdcl$_3$) δ 157.36, 146.44, 129.44, 119.47, 115.15, 113.91, 94.44, 75.83, 56.01, 31.84, 10.15.

b) Using aziridine organocatalyst 3:

Hexanes (20 mL), and diphenyl((R)-1-((S)-1-phenylethyl)aziridin-2-yl)methanol (100.0 mg, 0.3 mmol) were cooled to 0° C. before adding a 1 M solution of diethylzinc in hexanes (13.3 mL, 13.3 mmol) dropwise. Reaction mixture was stirred at 0° C. before the addition of aldehyde 1 (R=MOM, 1.00 g, 6.0 mmol) dropwise. After 20 h at 0° C. and 20 h at room temperature, reaction mixture was quenched with a saturated solution of $NH_4Cl$ (20 mL). After separating the layers, the aqueous fraction was extracted with EtOAc three times. Combined organic layers were washed with brine, dried over $Na_2SO_4$, and concentrated in vacuo. Crude product was purified by FCC ($SiO_2$, 20% EtOAc in hexanes) to obtain 2 (R=MOM, 1.14 g, 96.7% yield, 99.1% ee) as pale yellow oil.

Identical spectral properties as above in method (a).

(S)-1-(3-((benzyloxy)methoxy)phenyl)propan-1-ol (2,R=BOM)

Using aziridine organocatalyst 3:

Known diphenyl((R)-1-((S)-1-phenylethyl)aziridin-2-yl)methanol (45 mg, 0.137 mmol) and toluene (0.5 mL) were cooled to 0° C. before adding a 1 M solution of diethylzinc in hexanes (6 mL, 6 mmol) dropwise. A solution of aldehyde 1 (R=BOM, 658 mg, 2.43 mmol) in toluene (4.5 mL) was added dropwise. After 10 h at 0° C., followed by 14 h at room temperature, reaction mixture was quenched with a saturated solution of $NH_4Cl$ (20 mL). After separating the layers, the aqueous fraction was extracted with diethyl ether three times. Combined organic layers were washed with brine, dried over $Na_2SO_4$, and concentrated in vacuo. Crude product was purified by FCC ($SiO_2$, 10% EtOAc in hexanes) to obtain (S)-2 (R=BOM) as liquid (548 mg, 83% yield, >99% ee). $^1$H NMR (401 MHz, Chloroform-d) δ 7.38-7.23 (m, 6H), 7.08 (t, J=2.0 Hz, 1H), 7.01 (ddq, J=6.8, 4.2, 1.1 Hz, 2H), 5.31 (s, 2H), 4.74 (s, 2H), 4.58 (td, J=6.6, 3.4 Hz, 1H), 1.90-1.68 (m, 3H), 0.93 (t, J=7.4 Hz, 3H).

(R)-1-(3-(benzyloxy)phenyl)propan-1-ol (2,R=Bn)

Using N,N-Dibutyl-D-(+)-norephedrine ((+)-DBNE)

Aldehyde 1 (R=Bn, 50 mg, 0.24 mmol), toluene (3 mL), and N,N-Dibutyl-D-(+)-norephedrine (4 uL, 0.014 mmol) were cooled to 0° C. before adding a 1 M solution of diethylzinc in hexanes (0.5 mL, 0.5 mmol) dropwise over 20 minutes. After 20 h from 0° C. to room temperature, reaction mixture was quenched with a saturated solution of $NH_4Cl$ (5 mL). After separating the layers, the aqueous fraction was extracted with EtOAc three times. Combined organic layers were washed with brine, dried over $Na_2SO_4$, and concentrated in vacuo. Crude product was purified by FCC ($SiO_2$, 20% EtOAc in hexanes) to obtain (R)-2 (R=Bn, 47 mg, 81% yield, 95% B.R.S.M., 91% ee) as pale yellow oil. $^1$H NMR (400 MHz, Chloroform-d) δ 7.44 (d, J=7.4 Hz, 2H), 7.39 (td, J=7.2, 1.1 Hz, 2H), 7.35-7.30 (m, 1H), 7.27 (d, J=8.8 Hz, 1H), 7.02-6.99 (m, 1H), 6.96-6.92 (m, 1H), 6.89 (ddd, J=8.2, 2.5, 1.2 Hz, 1H), 5.07 (s, 2H), 4.58 (td, J=6.5, 3.4 Hz, 1H), 1.87-1.69 (m, 2H), 0.92 (td, J=7.4, 0.9 Hz, 3H) $^{13}$C NMR (100 MHz, cdcl$_3$) δ 158.91, 129.41, 128.53, 127.92, 127.48, 118.55, 113.77, 112.43, 75.88, 69.95, 31.80, 10.08.

(S)-1-(3-(benzyloxy)phenyl)propan-1-01 (2,R=Bn)

Using aziridine organocatalyst 3

Aldehyde 1 (R=Bn, 14.2 g, 66.8 mmol), toluene (35 mL), and diphenyl((S)-1-((S)-1-phenylethyl)aziridin-2-yl)methanol (1.32 g, 4.09 mmol) were cooled to 0° C. before adding a 1 M solution of diethylzinc in toluene (148 mL, 148 mmol) dropwise over 6 hours. Reaction mixture was allowed to warm to room temperature slowly. After 30 h, reaction mixture was quenched with a saturated solution of ammonium chloride ($NH_4Cl$) (150 mL). After separating the layers, the aqueous fraction was extracted with EtOAc three times. Combined organic layers were washed with brine, dried over $Na_2SO_4$, and concentrated in vacuo. Crude product was purified by FCC ($SiO_2$, 20% EtOAc in hexanes) to obtain (S)-2 (R=Bn, 16.2 g, quant. yield, 99.2% ee) as pale yellow oil.

Identical spectral properties as above using (+)-DBNE.

(1R,3S,3'S)-3,3'-diethyl-7,7'-bis(methoxymethoxy)-3H,3'H-1,1'-spirobi[isobenzofuran] (R,S,S-4, R=MOM)

Alcohol (R)-2 (22.84 g, 116.4 mmol) and toluene (PhMe) (330 mL) were cooled to 0° C. before addition of a 2.5 M solution n-Butyllithium in hexanes (44 mL over 15 min, then 50 mL over 1 h, 235.0 mmol). Reaction mixture was then warmed to room temperature. After 3 h, the resulting suspension was dissolved using 12 mL of tetrahydrofuran (THF) and cooled again to 0° C. Diethyl carbonate (7.7 mL, 63.5 mmol) was incorporated over 2 h at 0° C. Reaction mixture was allowed to warm slowly to room temperature overnight (12 h). Glacial acetic acid (100 mL) was then added slowly at room temperature. After 4 h at room temperature, reaction mixture was quenched with 500 mL of water, followed by careful addition of 100 g of $NaHCO_3$. After separating the layers, the aqueous fraction was extracted with DCM three times. Combined organic layers were washed with brine, dried over $Na_2SO_4$, and concentrated in vacuo. The mixture components were purified by FCC ($SiO_2$): 3.34 g of starting material 2 (14.6% recovery) were obtained at 15% EtOAc in hexanes, while 15.65 g of desired product 4 (R=MOM, 67.2% yield) were isolated at 25% EtOAc in hexanes as a pale yellow oil. Additionally, some intermediate isobenzofuranone 5 (2.43 g, 9.4% yield) was obtained at 35% EtOAc in hexanes as a pale yellow oil. $^1$H NMR (500 MHz, Chloroform-d) δ 7.29 (t, J=7.8 Hz, 2H), 6.88 (dd, J=7.9, 3.6 Hz, 4H), 5.40 (dd, J=7.4, 3.9 Hz, 2H), 4.95 (d, J=6.6 Hz, 2H), 4.82 (d, J=6.6 Hz, 2H), 3.07 (s, 6H), 1.98 (dtd, J=14.8, 7.3, 3.9 Hz, 2H), 1.86 (dq, J=14.3, 7.3 Hz, 2H), 1.04 (t, J=7.4 Hz, 6H). $^{13}$C NMR (126 MHz, cdcl$_3$) δ 152.44, 145.61, 130.58, 127.76, 113.99, 112.15, 93.29, 83.15, 55.60, 28.06, 9.74. ESI-HRMS Calcd. for $C_{23}H_{29}O_6^+$ 401.1964 [M+H]$^+$, found 401.1958.

(1S,3R,3'R)-7,7'-bis((benzyloxy)methoxy)-3,3'-diethyl-3H,3'H-1,1'-spirobi[isobenzofuran] (S,R,R-4, R=BOM)

Alcohol (R)-2 (R=BOM, 298 mg, 1.1 mmol) and PhMe (6 mL) were cooled to 0° C. before addition of a 2.2 M solution n-Butyllithium in hexanes (1.2 mL over 15 min, 2.6 mmol). Reaction mixture was stirred at 0° C. for 3 hours. Diethyl carbonate (80 uL, 0.68 mmol) was incorporated over 20 minutes at 0° C. Reaction mixture was allowed to warm slowly to room temperature overnight (12 h). Glacial acetic acid (1 mL) was then added slowly at room temperature. After 4 h at room temperature, reaction mixture was quenched with a saturated solution of $NaHCO_3$ (5 mL). After separating the layers, the aqueous fraction was extracted with EtOAc three times. Combined organic layers were washed with brine, dried over $Na_2SO_4$, and concentrated in vacuo. The mixture components were purified by FCC ($SiO_2$, 10% EtOAc in hexanes) to obtain (S,R,R-4) (R=BOM, 270 mg, 45% yield) as clear oil. $^1$H NMR (401 MHz, Chloroform-d) δ 7.34 (t, J=7.8 Hz, 2H), 7.28-7.24 (m, 6H), 7.04 (dd, J=6.6, 2.9 Hz, 4H), 6.99 (d, J=8.1 Hz, 2H), 6.94 (d, J=7.5 Hz, 2H), 5.44 (dd, J=7.4, 4.1 Hz, 2H), 5.06 (d, J=6.7 Hz, 2H), 4.88 (d, J=6.7 Hz, 2H), 4.28-4.16 (m, 4H), 1.88 (dq, J=14.8, 7.5 Hz, 4H), 1.06 (t, J=7.4 Hz, 6H). ESI-HRMS Calcd. for $C_{35}H_{37}O_6^+$ 553.2584 [M+H]$^+$, found 553.2583.

(1S,3R,3'R)-7,7'-bis(benzyloxy)-3,3'-diethyl-3H,3'H-1,1'-spirobi[isobenzofuran] (S,R,R-4, R=Bn)

Alcohol (R)-2 (R=Bn, 315 mg, 1.3 mmol) and PhMe (5 mL) were cooled to 0° C. before addition of a 2.2 M solution n-Butyllithium in hexanes (1.2 mL over 15 min, 2.6 mmol). Reaction mixture was stirred at 0° C. for 3 hours. Diethyl carbonate (80 uL, 0.68 mmol) was incorporated over 20 minutes at 0° C. Reaction mixture was allowed to warm slowly to room temperature overnight (12 h). Glacial acetic acid (1 mL) was then added slowly at room temperature. After 4 h at room temperature, reaction mixture was quenched with a saturated solution of NaHCO$_3$ (5 mL). After separating the layers, the aqueous fraction was extracted with EtOAc three times. Combined organic layers were washed with brine, dried over Na$_2$SO$_4$, and concentrated in vacuo. The mixture components were purified by FCC (SiO$_2$, 10% EtOAc in hexanes) to obtain (S,R,R-4) (R=Bn, 60 mg, 18.8% yield) as clear oil. $^1$H NMR (400 MHz, Chloroform-d) δ 7.38 (t, J=7.8 Hz, 2H), 7.19-7.02 (m, 6H), 6.83 (dd, J=14.9, 7.8 Hz, 4H), 6.75-6.62 (m, 4H), 5.39 (dd, J=7.2, 4.3 Hz, 2H), 5.00-4.80 (m, 4H), 1.87-1.59 (m, 4H), 0.86 (t, J=7.4 Hz, 6H). $^{13}$C NMR (100 MHz, cdcl$_3$) δ 154.21, 145.84, 136.62, 130.52, 127.97, 127.50, 127.15, 126.42, 115.83, 113.51, 110.36, 83.14, 68.86, 27.79, 9.64. ESI-HRMS Calcd. for $C_{33}H_{33}O_4^+$ 493.2373 [M+H]$^+$, found 493.2370.

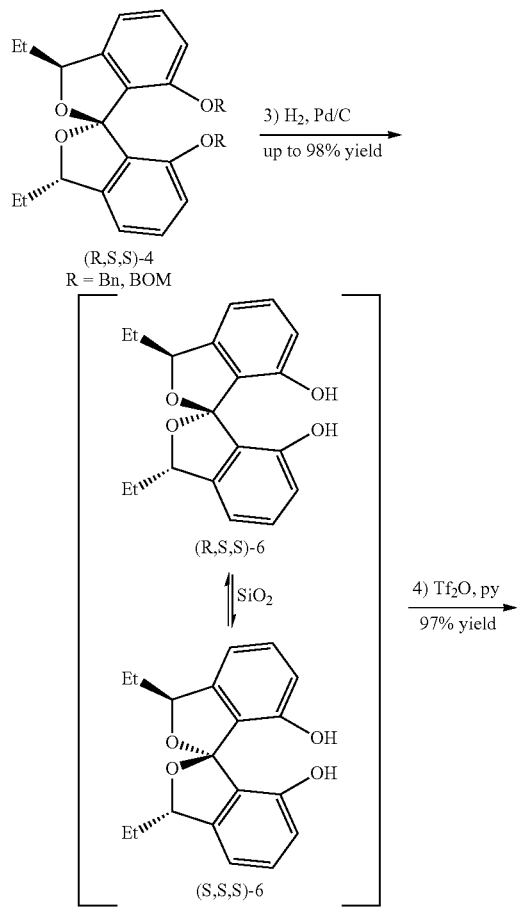

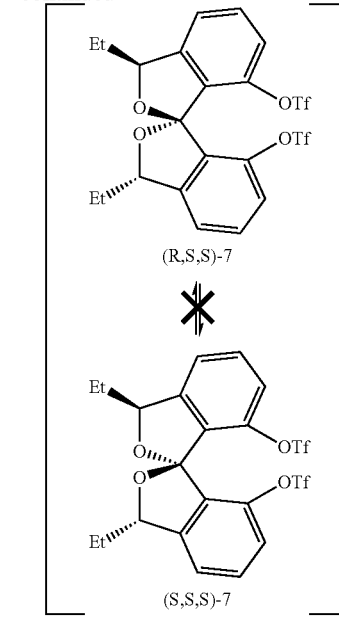

(1S,3S,3'S)-3,3'-diethyl-3H,3'H-1,1'-spirobi[isobenzofuran]-7,7'-diyl bis(trifluoromethanesulfonate) ((S,S,S)-7) from (R,S,S)-4 (R=MOM)

Spiroketal (R,S,S)-4 (R=MOM, 12.57 g, 7.0 mmol) and methanol (160 mL) were cooled to 0° C. before dropwise addition of acetyl chloride (1.0 mL, 14.1 mmol). Reaction mixture was then warmed to room temperature. After for 6 h, the volatiles were removed in vacuo, and the crude product was purified by FCC (SiO$_2$, 30% then 50% EtOAc in hexanes). Purified diol, DCM (150 mL), and pyridine (12.5 mL, 165.3 mmol) were cooled to 0° C. before addition of trifluoromethanesulfonic anhydride (12.0 mL, 71.5 mmol) over 30 min. Reaction mixture was then warmed to room temperature. After 1 h, a saturated aqueous solution of NaHCO$_3$ (150 mL) was added. After separating the layers, the aqueous phase was extracted with DCM twice. Combined organic layers were dried over Na$_2$SO$_4$ and concentrated in vacuo. Crude product was purified by a short column (SiO$_2$, 10% EtOAc in hexanes) to afford a mixture of triflates as an oil which solidified on cooling (15.8 g, 1:2.6:4.7 d.r. of (S,R,S)-7:(R,S,S)-7:(S,S,S)-7, 49.6% yield of desired (S,S,S)-7, 27.1% yield of also useful (R,S,S)-7).

The ditriflates can be separated by FCC (SiO$_2$, 4% EtOAc in hexanes), but for convenience we chose to do a chemical resolution (vide infra). The spectral characteristics of the isolated ditriflates are shown below:

(1R,3S,3'S)-3,3'-diethyl-3H,3'H-1,1'-spirobi[isobenzofuran]-7,7'-diyl bis(trifluoromethanesulfonate) ((R,S,S)-7)

$^1$H NMR (400 MHz, Chloroform-d) δ 7.53 (t, J=7.9 Hz, 2H), 7.30 (d, J=8.5 Hz, 4H), 5.36 (dd, J=8.5, 4.0 Hz, 2H), 2.05 (m, J=15.0, 7.5, 4.0 Hz, 2H), 1.97-1.82 (m, 2H), 1.11 (t, J=7.4 Hz, 6H). $^{19}$F NMR (376 MHz, cdcl$_3$) δ −74.57. $^{13}$C NMR (100 MHz, cdcl$_3$) δ 147.80, 144.92, 132.21, 129.82, 122.91, 120.81, 119.72, 119.13, 116.54, 113.33, 83.64, 27.39, 10.05. ESI-HRMS Calcd. for $C_{21}H_{19}F_6O_8S_2^+$ 577.0426 [M+H]$^+$, found 577.0415.

(1S,3S,3'S)-3,3'-diethyl-3H,3'H-1,1'-spirobi[isobenzofuran]-7,7'-diyl bis(trifluoromethanesulfonate) ((S,S,S)-7)

$^1$H NMR (400 MHz, Chloroform-d) δ 7.51 (t, J=7.9 Hz, 2H), 7.29 (d, J=7.5 Hz, 2H), 7.23 (d, J=8.2 Hz, 2H), 5.38 (dd, J=7.2, 4.5 Hz, 2H), 2.07-1.81 (m, 4H), 1.06 (t, J=7.4 Hz, 6H). $^{19}$F NMR (376 MHz, cdcl$_3$) δ −74.58. $^{13}$C NMR (100 MHz, cdcl$_3$) δ 147.33, 144.73, 132.07, 130.30, 122.92, 121.21, 119.74, 119.62, 119.60, 116.55, 114.51, 113.37, 84.77, 30.09, 9.45. ESI-HRMS Calcd. for $C_{21}H_{19}F_6O_8S_2^+$ 577.0426 [M+H]$^+$, found 577.0418.

(1R,3R,3'R)-3,3'-diethyl-3H,3'H-1,1-spirobi[isobenzofuran]-7,7'-dicarboxylic acid ((R,R,R)-8) from (R,R,R)-7+(S,R,R)-7+(R,S,R)-7

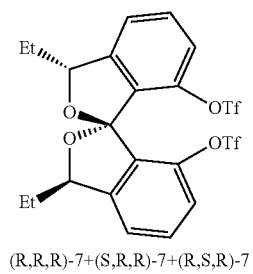

(R,R,R)-7+(S,R,R)-7+(R,S,R)-7

1. TEA, CO, MeOH
Pd(OAc)$_2$, dppp
DMSO, 70° C.
2. MeOH, KOH

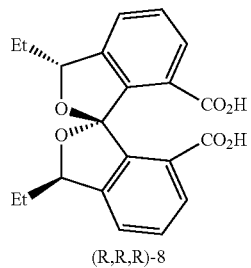

(R,R,R)-8

A flask in a glovebox was charged with a 1:2.5:6.9 mixture of ditriflates (R,S,R)-7:(S,R,R)-7:(R,R,R)-7 (6.65 g, 11.6 mmol), palladium(II) acetate (261 mg, 1.16 mmol), and 1,3-Bis(diphenylphosphino)propane (477 mg, 1.16 mmol). The flask was closed and taken outside the glovebox, and DMSO (90 mL), methanol (60 mL) and triethylamine (26 mL, 197 mmol) were added to the flask. The reaction mixture was then saturated with CO and stirred under 35 psi CO at 70° C. for full conversion. After cooling to room temperature, the reaction mixture was filtered through celite and concentrated in vacuo. The crude was directly used for the next step.

The crude compound was added to a solution of methanol (MeOH) (40 mL) and 30% aqueous potassium hydroxide (KOH) (40 mL) and stirred at refluxing for 10 h. The resulting mixture was cooled to room temperature, diluted with water (200 mL) and adjusted pH to 4-5 with 6 M hydrochloric acid (HCl), and extracted with ethyl acetate (120 mL) three times. The combined organic layer was washed with water and saturated brine, dried over anhydrous MgSO$_4$, and concentrated. The crude compound was purified by FCC (SiO$_2$, 0→50% EtOAc in hexanes) to obtain 2.82 g of oil product ((R,R,R)-8) (66% yield over 2 steps).

$^1$H NMR (400 MHz, CDCl$_3$) δ 7.91-7.82 (m, 2H), 7.48-7.40 (m, 4H), 5.18 (dd, J=7.4, 4.1 Hz, 2H), 2.03-1.78 (m, 4H), 1.07 (t, J=7.4 Hz, 6H). $^{13}$C NMR (100 MHz, cdcl3) δ 170.56, 145.72, 140.95, 130.82, 128.87, 125.63, 124.60, 118.20, 84.43, 30.16, 9.78).

(1R,3R,3'R)-3,3'-diethyl-N7,N7'-bis((R)-2-hydroxy-1-phenylethyl)-3H,3'H-1,1'-spirobi[isobenzofuran]-7,7'-dicarboxamide ((R,R,R)-9) from (R,R,R)-8

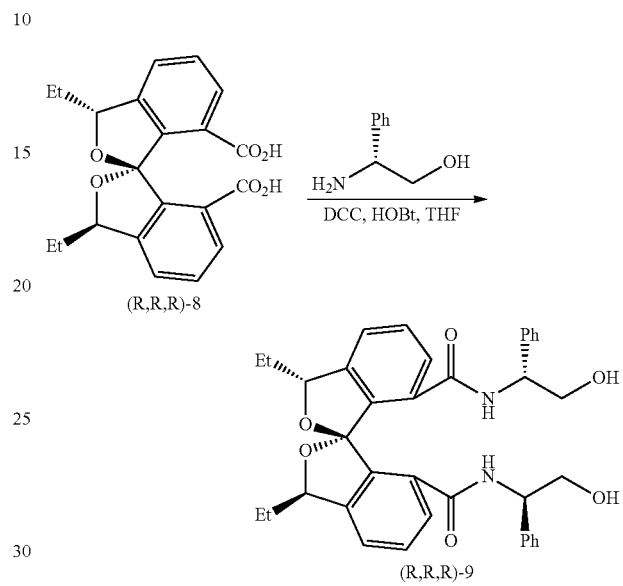

A solution of (R,R,R)-8 (500 mg, 1.36 mmol), dicyclohexyl carbodiimide (DCC) (1.20 g, 5.71 mmol), benzotriazol-1-ol (HOBt) (408 mg, 2.99 mmol) and (S)-2-amino-2-phenylethanol (408 g, 1.99 mmol) in dry THF was cooled to −5° C. and stirred for 1 hour. The mixture was allowed to warm to room temperature and the mixture was stirred overnight. The resulting mixture was concentrated under reduced pressure, and the residue was purified by FCC (ethyl acetate) to obtain (R,R,R)-9 (560 mg, 68%) as white solids.

$^1$H NMR (401 MHz, Chloroform-d) δ 7.41-7.33 (m, 4H), 7.24-7.16 (m, 8H), 7.08 (dd, J=7.1, 2.4 Hz, 4H), 4.52 (ddd, J=17.9, 8.5, 4.8 Hz, 4H), 3.52 (dd, J=11.7, 5.4 Hz, 2H), 3.23 (dd, J=11.7, 3.8 Hz, 2H), 1.89-1.68 (m, 4H), 0.96 (t, J=7.4 Hz, 6H). ESI-HRMS Calcd. for $C_{37}H_{39}N_2O_6$+607.2808 [M+H]$^+$, found 607.2793.

(1S,3R,3'R)-3,3'-diethyl-N7,N7'-bis((R)-2-hydroxy-1-phenylethyl)-3H,3'H-1,1'-spirobi[isobenzofuran]-7,7'-dicarboxamide ((S,R,R)-9) from (R,R,R)-8

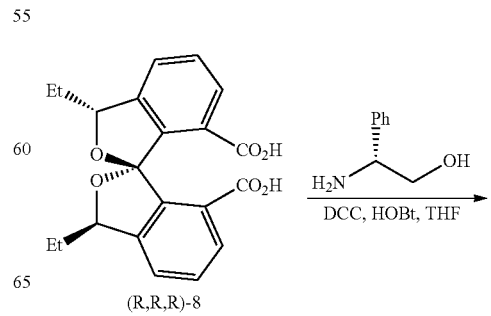

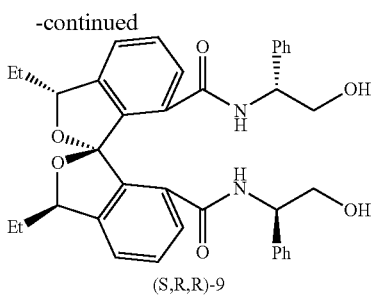

(S,R,R)-9

A solution of (R,R,R)-8 (1.50 g, 4.08 mmol), dicyclohexyl carbodiimide (3.60 g, 17.1 mmol), benzotriazol-1-ol (1.22 g, 8.97 mmol) and (S)-2-amino-2-phenylethanol (1.22 g, 8.97 mmol) in dry THF was cooled to −5° C. and stirred for 1 hour. The mixture was allowed to warm to room temperature and the mixture was stirred overnight. The reaction mixture was quenched by 5 ml of 1N HCl, diluted with water and extracted with ethyl acetate (20 mL*3) and diethyl ether (20 mL*3). The combined organic layer was concentrated under reduced pressure, and the residue was purified by FCC (ethyl acetate) to obtain (S,R,R)-9 (1.94 g, 47%) as a white solids.

$^1$H NMR (700 MHz, Chloroform-d) δ 7.41 (d, J=7.4 Hz, 2H), 7.38-7.35 (m, 2H), 7.32-7.23 (m, 8H), 7.10 (d, J=6.8 Hz, 2H), 7.06-7.02 (m, 2H), 4.96 (dd, J=7.7, 5.2 Hz, 2H), 4.63 (td, J=6.7, 4.1 Hz, 2H), 3.42 (dd, J=11.5, 4.0 Hz, 2H), 3.29 (dd, J=11.3, 6.8 Hz, 2H), 3.09 (s, 2H), 1.97-1.84 (m, 4H), 1.05 (t, J=7.3 Hz, 6H). ESI-HRMS Calcd. for $C_{37}H_{39}N_2O_6^+$ 607.2808 [M+H]$^+$, found 607.2793.

(4R,4'R)-2,2'-((1R,3R,3'R)-3,3'-diethyl-3H,3'H-1,1'-spirobi[isobenzofuran]-7,7'-diyl)bis(4-phenyl-4,5-dihydrooxazole) ((R,R,R)-10) from (R,R,R)-9

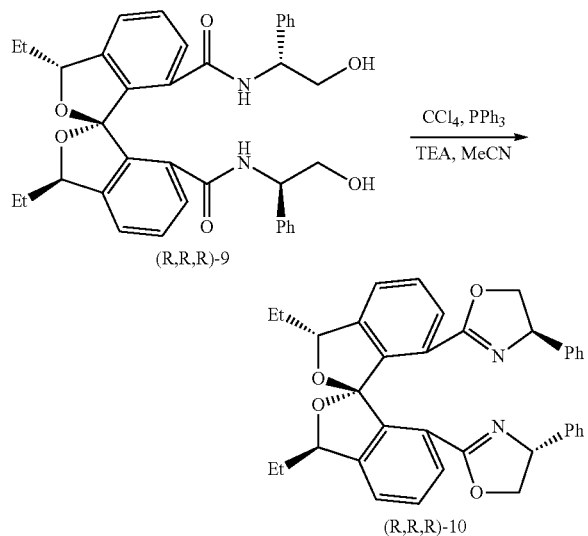

A solution of (R,R,R)-9 (550 mg, 0.92 mmol), triphenylphosphine (963 mg, 3.68 mmol), triethylamine (0.52 mL, 3.68 mmol), and tetrachloromethane (0.36 mL, 3.68 mmol) in dry acetonitrile was stirred over night at room temperature. After concentrating in vacuo, the residue was dissolved in dichloromethane (CH$_2$Cl$_2$), washed with water, dried over anhydrous magnesium sulfate, and then concentrated in vacuo. The crude product was purified by chromatography on silica gel column (ethyl acetate/petroleum ether=1:3) to afford 513 mg of (R,R,R)-10 as white solids (96% yield).

$^1$H NMR (401 MHz, Chloroform-d) δ 8.09-7.83 (m, 2H), 7.38-7.24 (m, 10H), 7.09-6.97 (m, 4H), 5.18 (dd, J=7.2, 4.8 Hz, 2H), 4.90 (t, J=9.8 Hz, 2H), 4.37 (dd, J=10.1, 8.3 Hz, 2H), 3.28 (dd, J=9.5, 8.3 Hz, 2H), 2.09-1.92 (m, 4H), 1.17 (t, J=7.4 Hz, 6H). ESI-HRMS Calcd. for $C_{37}H_{35}N_2O_4^+$ 571.2597 [M+H]$^+$, found 571.2571.

(4R,4'R)-2,2'-((1R,3R,3'R)-3,3'-diethyl-3H,3'H-1,1'-spirobi[isobenzofuran]-7,7'-diyl)bis(4-phenyl-4,5-dihydrooxazole) ((S,R,R)-10) from (S,R,R)-9

A solution of (S,R,R)-9 (234 mg, 0.38 mmol), triphenylphosphine (406 mg, 1.55 mmol), triethylamine (0.22 mL, 1.55 mmol), and tetrachloromethane (0.15 mL, 1.55 mmol) in dry acetonitrile was stirred over night at room temperature. After concentrating in vacuo, the residue was dissolved in CH$_2$Cl$_2$, washed with water, dried over anhydrous magnesium sulfate, and then concentrated in vacuo. The crude product was purified by chromatography on silica gel column (ethyl acetate/petroleum ether=1:3) to afford 105 mg of (S,R,R)-10 as white solids (47% yield).

$^1$H NMR (400 MHz, Chloroform-d) δ 7.94 (d, J=7.6 Hz, 2H), 7.33 (t, J=7.6 Hz, 2H), 7.26-7.19 (m, 8H), 6.99-6.92 (m, 4H), 5.17 (dd, J=7.5, 4.3 Hz, 2H), 5.01 (dd, J=10.2, 7.8 Hz, 2H), 3.92 (dd, J=10.2, 8.2 Hz, 2H), 3.81 (t, J=8.1 Hz, 2H), 2.01-1.88 (m, 4H), 1.11 (t, J=7.3 Hz, 6H). ESI-HRMS Calcd. for $C_{37}H_{35}N_2O_4^+$ 571.2597 [M+H]$^+$, found 571.2571.

SPIROL Equilibration Studies and Isomer Ratio

The isomeric ratio of the free SPIROL after deprotection of MOM groups was variable, because epimerization happens in silica-containing solutions and the d.r. is dependent on the solvent. SiO$_2$ in PhMe lightly favors equilibration towards the (R,S,S)-6 isomer, while EtOAc/Hexanes mixtures slightly favor the (S,S,S)-6 isomer.

A vial was charged with a 2.9:1 (S,S,S)-6:(R,S,S)-6 mixture (300 mg), PhMe (3 mL), and SiO$_2$ (3.0 g). After stirring at room temperature for 4 days, the diol mixture was recovered quantitatively by filtration and concentration in vacuo, with a 2.4:1 (S,S,S)-6:(R,S,S)-6 d.r.

Similarly, a vial was charged with a 2.4:1 (S,S,S)-6:(R,S,S)-6 mixture (100 mg), EtOAc (0.5 mL), hexanes (0.5 mL), and SiO$_2$ (1.0 g). After stirring at room temperature for 2 days, the diol mixture was recovered quantitatively by filtration and concentration in vacuo, with a 1.2:1 (S,S,S)-6:(R,S,S)-6 d.r.

The ((S,R,S)-6 epimer is undesired and removed in later steps. A much better second-generation route involves using Bn-protecting groups. The deprotection is then carried out by hydrogenolysis under standard conditions to afford (R,S,S)-6 cleanly, as described below.

(1S,3R,3'R)-3,3'-diethyl-3H,3'H-1,1-spirobi[isobenzofuran]-7,7'-diol (S,R,R-6)

Spiroketal (S,R,R)-4 (10 mg, 0.02 mmol), Pd/C (2.2 mg, 0.0020 mmol) and MeOH (0.3 mL) were mixed together at room temperature. The reaction container was purged with N$_2$ and then H$_2$, and the mixture was stirred under 1 atm of H$_2$ for 2 hours. Reaction mixture was filtered and volatiles were removed in vacuo. Crude product was purified by FCC (SiO2, 20% EtOAc in hexanes) to obtain (S,R,R)-6 (6.2 mg, quant. yield). 1H NMR (401 MHz, Chloroform-d) δ 7.34 (t, J=7.8 Hz, 2H), 6.85 (d, J=7.5 Hz, 2H), 6.77 (d, J=8.1 Hz, 2H), 5.40 (dd, J=6.8, 4.1 Hz, 2H), 4.66-4.52 (m, 2H), 2.05 (m, J=14.8, 7.6, 3.7 Hz, 2H), 1.80 (m, 2H), 1.00 (t, J=7.4 Hz, 6H).

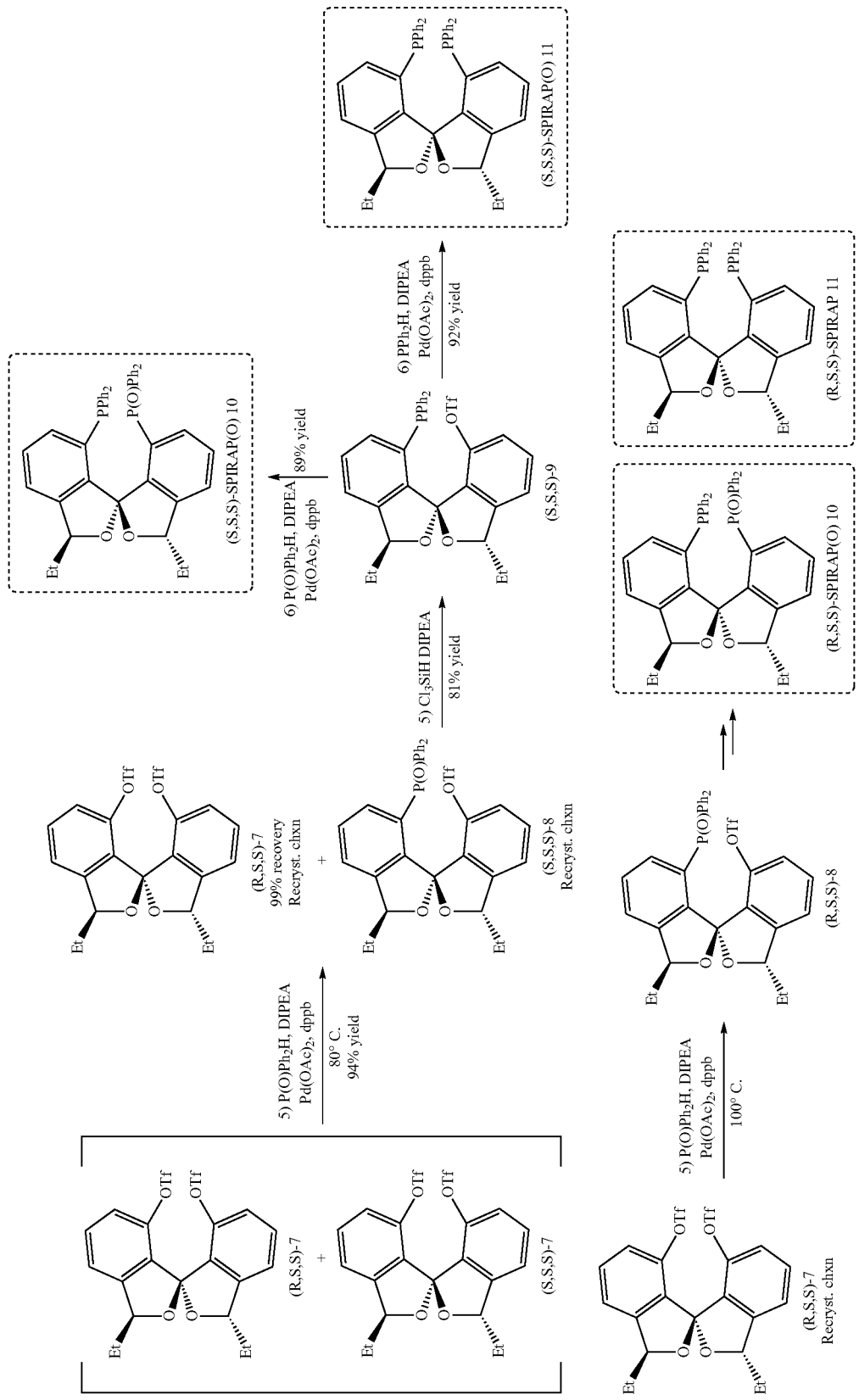

(1S,3S,3'S)-7'-(diphenylphosphoryl)-3,3'-diethyl-3H, 3'H-1,1'-spirobi[isobenzofuran]-7-yl trifluoromethanesulfonate ((S,S,S)-8)

A flask in the glovebox was charged with a 1:2.6:4.7 mixture of ditriflates (S,R,S)-7:(R,S,S)-7:(S,S,S)-7 (12.624 g, 21.86 mmol), palladium(II) acetate (245 mg, 1.09 mmol), 1,4-Bis(diphenylphosphino)butane (466 mg, 1.09 mmol), and diphenylphosphine oxide (4.861 g, 24.04 mmol). The flask was taken outside the glovebox, and DMSO (85 mL) and N,N-Diisopropylethylamine (9.5 mL, 54.64 mmol) were added. Reaction mixture was then stirred at room temperature for 1 h, before being heated to 80° C. After 8 h, reaction mixture was cooled to room temperature and partitioned between EtOAc (60 mL) and a half saturated aqueous solution of $NaHCO_3$ (60 mL). After separating the layers, the aqueous phase was extracted with EtOAc twice. Combined organic layers were washed with brine, dried over $Na_2SO_4$, and concentrated in vacuo. Crude product was purified by FCC ($SiO_2$, 10→50% EtOAc in hexanes) to yield two fractions. At 10% EtOAc in hexanes, a mixture of (S,R,S)-7 and (R,S,S)-7 was obtained (1:4.2 d.r., 3.88 g of useful (R,S,S)-7, 99.0% recovery based on starting (R,S,S)-7). At 50% EtOAc in hexanes, a mixture of epimeric product (S,R,S)-8 and desired phosphine oxide (S,S,S)-8 was obtained (1:12.6 d.r., 7.34 g of desired (S,S,S)-8, 93.8% yield based on starting (S,S,S)-7).

The desired product was further purified by two recrystallizations from cyclohexane with excellent recovery. The first recrystallization of 5.71 g of the product mixture gave 5.33 g of a 1:26 mixture of epimeric product (S,R,S)-8 and desired phosphine oxide (S,S,S)-8, respectively (97% recovery of product). Chiral HPLC analysis showed that the desired product was enantioenriched to >99% ee. A second recrystallization of 5.02 g of this mixture produced 4.58 g of almost pure (S,S,S)-8 (1:65 with respect to (S,R,S)-8) (93% recovery of product), as a white foam. $^1$H NMR (500 MHz, Chloroform-d) δ 7.52-7.42 (m, 4H), 7.42-7.31 (m, 4H), 7.27-7.21 (m, 2H), 7.21-7.10 (m, 4H), 7.02 (dd, J=13.9, 7.5 Hz, 1H), 6.41 (dd, J=7.1, 1.5 Hz, 1H), 5.56 (dd, J=7.1, 4.7 Hz, 1H), 5.28 (dd, J=7.2, 5.0 Hz, 1H), 1.92 (m, J=13.5, 6.3 Hz, 3H), 1.83 (m, J=14.3, 7.2 Hz, 1H), 1.06 (t, J=7.4 Hz, 3H), 0.99 (t, J=7.4 Hz, 3H). $^{13}$C NMR (126 MHz, cdcl$_3$) δ 148.85, 146.47, 146.40, 144.19, 141.69, 141.64, 133.80, 133.77, 133.70, 132.93, 132.51, 132.14, 132.07, 131.68, 131.55, 131.53, 131.31, 131.25, 131.20, 131.18, 131.01, 130.94, 128.59, 128.49, 128.22, 128.19, 128.12, 128.09, 127.40, 125.38, 125.36, 121.89, 120.41, 119.34, 118.47, 116.80, 116.25, 85.27, 83.49, 30.60, 29.71, 26.90, 9.88, 9.66. $^{19}$F NMR (471 MHz, cdcl$_3$) δ −75.05. $^{31}$P NMR (202 MHz, cdcl$_3$) δ 28.57. ESI-HRMS Calcd. for $C_{32}H_{29}F_3O_6PS^+$ 629.1375 [M+H]$^+$, found 629.1366.

(1R,3S,3'S)-7'-(diphenylphosphoryl)-3,3'-diethyl-3H, 3'H-1,1'-spirobi[isobenzofuran]-7-yl trifluoromethanesulfonate ((R,S,S)-8)

Recovered (R,S,S)-8 from the reaction above was recrystallized from cyclohexane and then resubjected to the same reaction conditions (3.94 g, 6.85 mmol), except reaction mixture was heated to 100° C. for 24 h. Reaction mixture was cooled to room temperature, and diluted with EtOAc After separating the layers, the aqueous phase was extracted with EtOAc twice. Combined organic layers were washed with brine, dried over $Na_2SO_4$, and concentrated in vacuo. Crude product was purified by FCC ($SiO_2$, 10→50% EtOAc in hexanes) to yield two fractions. At 5% EtOAc in hexanes, some impure starting material was recovered (98.9 mg). At 40% EtOAc in hexanes, the desired product was obtained as white foam (3.15 g, 73% yield). $^1$H NMR (401 MHz, Chloroform-d) δ 7.51-7.28 (m, 13H), 7.15 (dd, J=10.0, 8.0 Hz, 2H), 7.06 (dd, J=13.8, 7.5 Hz, 1H), 5.33 (dd, J=8.2, 4.0 Hz, 1H), 5.14 (dd, J=10.0, 3.5 Hz, 1H), 2.03 (m, J=14.9, 7.4, 4.1 Hz, 1H), 1.88 (m, J=14.4, 7.3 Hz, 1H), 1.70 (m, J=15.0, 7.5, 3.7 Hz, 1H), 1.60-1.44 (m, 1H), 1.08 (t, J=7.4 Hz, 3H), 0.53 (t, J=7.4 Hz, 3H). $^{31}$P NMR (162 MHz, cdcl$_3$) δ 29.90. $^{19}$F NMR (377 MHz, cdcl$_3$) δ −75.08.

(1S,3S,3'S)-7'-(diphenylphosphanyl)-3,3'-diethyl-3H, 3'H-1,1'-spirobi[isobenzofuran]-7-yl trifluoromethanesulfonate ((S,S,S)-9)

Phosphine oxide (S,S,S)-8 (4.95 g, 7.88 mmol), PhMe (80 mL), and Diisopropylethylamine (55 mL, 316.8 mmol) were cooled to 0° C. before addition of trichlorosilane (12.5 mL, 126.1 mmol) over 10 min. The flask was sealed with a glass stopped and heated to 80° C. After 20 h, the mixture was cooled to room temperature and quenched carefully by transferring it to a flask containing a saturated aqueous solution of $NaHCO_3$ (120 mL) at 0° C., with diethyl ether washings. Crude product was filtered through Celite with diethyl ether washings, and the filtrate was dried over $Na_2SO_4$ and concentrated in vacuo. Crude product was purified by FCC ($SiO_2$, 5% EtOAc in hexanes) to afford (S,S,S)-9 (3.89 g, 80.7% yield) as white foam. $^1$H NMR (500 MHz, Chloroform-d) δ 7.32 (t, J=7.5 Hz, 1H), 7.29-7.20 (m, 6H), 7.17 (d, J=7.5 Hz, 1H), 7.13 (td, J=7.5, 1.5 Hz, 2H), 7.07 (td, J=7.5, 2.0 Hz, 2H), 6.89 (dd, J=7.4, 4.6 Hz, 1H), 6.85 (td, J=7.9, 1.4 Hz, 2H), 6.62 (d, J=8.1 Hz, 1H), 5.35 (td, J=6.8, 4.6 Hz, 2H), 1.96 (m, J=16.9, 14.0, 5.9 Hz, 2H), 1.87 (m, J=14.2, 7.2, 4.6 Hz, 2H), 1.06 (t, J=7.3 Hz, 3H), 1.00 (t, J=7.3 Hz, 3H). ESI-HRMS Calcd. for $C_{32}H_{23}F_3O_5PS^+$ 613.1425 [M+H]$^+$, found 613.1419. $^{13}$C NMR (126 MHz, cdcl$_3$) δ 147.39, 147.37, 144.53, 143.68, 143.62, 142.55, 142.35, 137.03, 136.93, 135.49, 135.41, 133.96, 133.94, 133.63, 133.49, 133.46, 133.33, 132.58, 132.56, 132.42, 131.46, 129.59, 128.42, 128.20, 128.17, 128.12, 128.00, 127.95, 122.04, 120.56, 119.35, 118.87, 116.81, 116.51, 116.49, 84.66, 84.61, 84.05, 30.47, 29.70, 9.64, 9.43. $^{19}$F NMR (471 MHz, Chloroform-d) δ −74.90. $^{31}$P NMR (202 MHz, cdcl$_3$) δ −18.88.

(1R,3S,3'S)-7'-(diphenylphosphanyl)-3,3'-diethyl-3H,3'H-1,1'-spirobi[isobenzofuran]-7-yl trifluoromethanesulfonate ((R,S,S)-9)

Same procedure as above for (S,S,S)-9, but using (R,S,S)-8 (1.98 g, 3.1 mmol). The product was obtained as white foam (808 mg, 42% yield). $^1$H NMR (401 MHz, Chloroform-d) δ 7.46 (t, J=7.9 Hz, 1H), 7.36 (t, J=7.4 Hz, 1H), 7.33-7.18 (m, 8H), 7.15-7.05 (m, 3H), 7.00-6.91 (m, 3H), 5.33 (dd, J=8.6, 4.1 Hz, 1H), 5.20 (dd, J=10.0, 3.4 Hz, 1H), 2.03 (m, J=14.2, 7.4, 5.0 Hz, 1H), 1.90 (m, J=14.6, 7.0 Hz, 1H), 1.77 (m, J=13.9, 7.4, 3.6 Hz, 1H), 1.52-1.40 (m, 1H), 1.12 (t, J=7.5 Hz, 3H), 0.69 (t, J=7.4 Hz, 3H). $^{31}$P NMR (162 MHz, cdcl$_3$) δ −21.55. $^{19}$F NMR (377 MHz, cdcl$_3$) δ −74.64.

((1S,3S,3'S)-7'-(diphenylphosphanyl)-3,3'-diethyl-3H,3'H-1,1'-spirobi[isobenzofuran]-7-yl)diphenylphosphine oxide ((S,S,S)-SPIRAP(O) (S,S,S)-10)

A flask in the glovebox was charged with phosphine (S,S,S)-9 (3.89 g, 6.35 mmol), palladium(II) acetate (71.3 mg, 0.32 mmol), 1,4-Bis(diphenylphosphino)butane (135.4 mg, 0.32 mmol), and diphenylphosphine oxide (2.57 g, 12.7 mmol). The flask was taken outside the glovebox, and DMSO (25 mL) and N,N-Diisopropylethylamine (5.5 mL, 31.56 mmol) were added. Reaction mixture was then stirred at room temperature for 1 hour before being then heated to 100° C. After 2 h, reaction mixture was cooled down to room temperature and partitioned between EtOAc (160 mL) and a half saturated aqueous solution of NaHCO$_3$ (160 mL). After separating the layers, the aqueous phase was extracted with EtOAc twice. Combined organic layers were washed with brine, dried over Na$_2$SO$_4$, and concentrated in vacuo. Crude was purified by FCC (SiO$_2$, 20→30% EtOAc in hexanes) to yield (S,S,S)-SPIRAP(O) ((S,S,S)-10)(3.95 g, 93.5% yield) as white foam. $^1$H NMR (700 MHz, Chloroform-d) δ 7.45 (td, J=6.3, 2.6 Hz, 1H), 7.41-7.29 (m, 6H), 7.29-7.13 (m, 13H), 7.07 (td, J=7.3, 2.1 Hz, 2H), 7.02 (td, J=7.7, 1.7 Hz, 2H), 6.87 (dd, J=7.5, 4.8 Hz, 1H), 6.71 (dd, J=13.9, 7.5 Hz, 1H), 5.35 (t, J=5.2 Hz, 1H), 4.71 (dd, J=8.2, 3.8 Hz, 1H), 1.93 (m, J=14.8, 7.5, 3.8 Hz, 1H), 1.79 (m, J=14.0, 6.9 Hz, 1H), 1.72 (m, J=11.4, 3.4 Hz, 1H), 1.64 (m, J=14.3, 7.4 Hz, 1H), 0.86 (t, J=7.3 Hz, 3H), 0.75 (t, J=7.3 Hz, 3H). $^{13}$C NMR (176 MHz, cdcl$_3$) δ 146.70, 146.55, 146.26, 146.24, 146.21, 146.19, 144.53, 144.51, 144.50, 143.64, 143.60, 138.60, 138.53, 136.55, 136.48, 134.76, 134.17, 134.16, 134.06, 133.46, 133.42, 133.40, 133.24, 133.13, 133.05, 132.87, 132.36, 132.31, 131.56, 131.51, 131.08, 131.07, 131.03, 131.01, 130.99, 130.93, 128.79, 128.29, 128.22, 127.95, 127.93, 127.89, 127.86, 127.81, 127.76, 127.74, 127.72, 127.65, 127.27, 124.65, 124.64, 121.46, 118.68, 84.29, 83.26, 83.21, 29.93, 29.54, 9.85, 8.82. $^{31}$P NMR (283 MHz, Chloroform-d) δ 28.63, −18.52. ESI-HRMS Calcd. for C$_{43}$H$_{39}$O$_3$P$_2$$^+$ 665.2374 [M+H]$^+$, found 665.2366.

((1R,3S,3'S)-7'-(diphenylphosphanyl)-3,3'-diethyl-3H,3'H-1,1'-spirobi[isobenzofuran]-7-yl)diphenylphosphine oxide ((R,S,S)-SPIRAP(0) (R,S,S)-10)

Same procedure as above for (S,S,S)-10, but using (R,S,S)-9 (748 mg, 1.30 mmol). The product was obtained as white foam (724 mg, 89% yield). $^1$H NMR (500 MHz, Chloroform-d) δ 7.50-7.16 (m, 20H), 7.14-6.99 (m, 5H), 6.94 (dd, J=13.9, 7.5 Hz, 1H), 5.18 (dd, J=10.0, 3.5 Hz, 1H), 5.10 (dd, J=10.0, 3.4 Hz, 1H), 1.80 (ddd, J=14.2, 7.4, 3.8 Hz, 1H), 1.66 (ddd, J=14.3, 7.4, 3.5 Hz, 1H), 1.40 (ddd, J=13.8, 9.7, 6.9 Hz, 1H), 0.83 (t, J=7.4 Hz, 3H), 0.44 (t, J=7.4 Hz, 3H). $^{31}$P NMR (202 MHz, cdcl$_3$) δ 29.76, −22.10.

((1S,3S,3'S)-3,3'-diethyl-3H,3'H-1,1'-spirobi[isobenzofuran]-7,7'-diyl)bis(diphenylphosphane) ((S,S,S)-SPIRAP (S,S,S)-11) from monotriflate (S,S,S)-9

A Schlenk flask was charged with palladium(II) acetate (36.6 mg, 0.163 mmol) and 1,4-Bis(diphenylphosphino) butane (76.6 mg, 0.180 mmol). DMF (3.0 mL) and diisopropylethylamine (1.8 mL, 10.3 mmol) were added. Solution was stirred at room temperature. After 1 h, diphenyl phosphine (850 μL, 4.89 mmol) was added. After 5 min, monotriflate (S,S,S)-9 (1.000 g, 1.632 mmol) was added as a solution in DMF (3.5 mL, including washings). The sealed flask was heated to 100° C. After 24 h, volatiles were removed under N$_2$ flow. Crude product was purified by FCC (SiO$_2$, 0→15%→30% DCM in hexanes) to yield (S,S,S)-SPIRAP ((S,S,S)-11)(977 mg, 92.3% yield) as white solid. $^1$H NMR (700 MHz, Chloroform-d) δ 7.30 (t, J=7.5 Hz, 2H), 7.23 (tq, J=13.7, 7.6 Hz, 10H), 7.17-7.10 (m, 4H), 7.06 (td, J=7.5, 1.8 Hz, 4H), 6.89 (dd, J=7.5, 4.5 Hz, 2H), 6.83 (t, J=7.4 Hz, 4H), 4.96 (dd, J=6.8, 4.3 Hz, 2H), 1.86 (m, J=14.6, 7.3, 4.1 Hz, 2H), 1.76 (m, J=14.3, 7.2 Hz, 2H), 0.87 (t, J=7.3 Hz, 6H). $^{13}$C NMR (176 MHz, cdcl$_3$) δ 145.51, 145.49, 145.36, 145.34, 144.09, 144.07, 144.05, 144.03, 138.22, 138.15, 136.81, 136.74, 134.11, 133.99, 133.72, 133.71, 133.13, 133.02, 132.59, 132.48, 129.12, 128.23, 128.02, 127.98, 127.93, 127.85, 127.82, 127.76, 121.54, 118.55, 83.29, 83.25, 29.76, 9.32. $^{31}$P NMR (283 MHz, cdcl$_3$) δ −18.71. ESI-HRMS Calcd. for C$_{43}$H$_{39}$O$_2$P$_2$$^+$ 649.2425 [M+H]$^+$, found 649.2417.

((1R,3S,3'S)-3,3'-diethyl-3H,3'H-1,1'-spirobi[isobenzofuran]-7,7'-diyl)bis(diphenylphosphane) ((R,S,S)-SPIRAP (R,S,S)-11) from monotriflate (R,S,S)-9

Same procedure as above for (S,S,S)-11, but using (R,S,S)-9 (560 mg, 1.30 mmol). The product was obtained as white foam (428 mg, 72% yield). $^1$H NMR (500 MHz, Chloroform-d) δ 7.36 (t, J=7.5 Hz, 2H), 7.30-7.15 (m, 16H), 7.04-6.89 (m, 9H), 5.13 (dd, J=10.0, 3.5 Hz, 2H), 1.69 (m, J=13.8, 7.4, 3.6 Hz, 2H), 1.28 (m, J=14.1, 7.0, 2.5 Hz, 2H), 0.65 (t, J=7.4 Hz, 6H). $^{31}$P NMR (202 MHz, cdcl$_3$) δ −21.02.

Synthesis of SPIROL-Derived Diphosphinites (SPIRAPO)

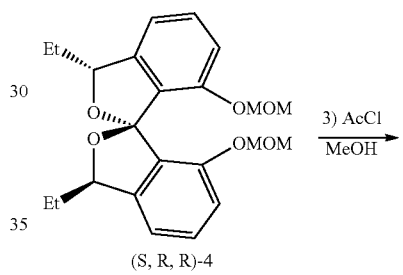

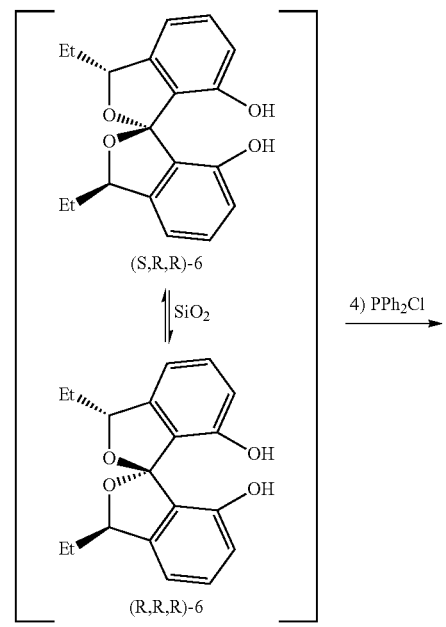

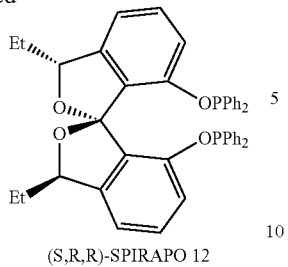

(S,R,R)-SPIRAPO 12

+

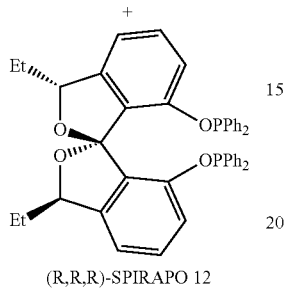

(R,R,R)-SPIRAPO 12

((((1S,3R,3'R)-3,3'-diethyl-3H,3'H-1,1'-spirobi[isobenzofuran]-7,7'-diyl)bis(oxy))bis(diphenylphosphane) ((S,R,R)-SPIRAPO-12) from (S,R,R)-4 (R=MOM)

Spiroketal (S,R,R)-4 (R=MOM, 490 Mg, 1.2 mmol) and methanol (2.4 mL) were cooled to 0° C. before dropwise addition of acetyl chloride (17 uL, 0.24 mmol). Reaction mixture was then warmed to room temperature. After for 6 h, the volatiles were removed in vacuo, and the crude product was purified by FCC (SiO2, 20% EtOAc in hexanes). Purified diol and 4-Dimethylaminopyridine (14.8 mg, 0.12 mmol) were dissolved into DCM (15 mL) at room temperature before addition of triethylamine (1.58 mL, 12.2 mmol) and chlorodiphenylphosphine (0.56 mL, 3.0 mmol) over 30 min. Reaction volatiles were removed in vacuo, and the crude product was purified by FCC (SiO$_2$ treated with 5% TEA, 5%→9% EtOAc in hexanes) to afford (S,R,R)-12 (215 mg, 26% yield) as white foam. $^1$H NMR (399.54 MHz, CDCl$_3$) δ 7.31-7.21 (m, 14H), 7.14 (t, J=7.4 Hz, 2H), 7.06 (ddd, J=10.4, 7.1, 5.3 Hz, 6H), 6.97-6.90 (m, 4H), 6.86-6.81 (m, 2H), 5.26 (dd, J=8.2, 4.2 Hz, 2H), 1.57 (hd, J=7.5, 4.2 Hz, 2H), 1.41 (dt, J=14.3, 7.5 Hz, 2H), 0.87 (t, J=7.4 Hz, 6H) $^{13}$C NMR (100 MHz, cdcl$_3$) δ 152.36, 152.27, 146.31, 140.11, 139.92, 139.88, 139.72, 130.73, 130.59, 130.49, 129.74, 129.63, 129.52, 128.89, 128.39, 128.31, 128.25, 128.18, 115.33, 115.17, 115.09, 114.69, 82.94, 28.02, 10.25 $^{31}$P NMR (161.75 MHz, CDCl$_3$) δ 105.24 ESI-HRMS Calcd. for C$_{43}$H$_{39}$O$_4$P$_2{}^+$681.2317 [M+H]$^+$, found 681.2316.

Ir-Catalyzed Asymmetric Hydroarylation

A)

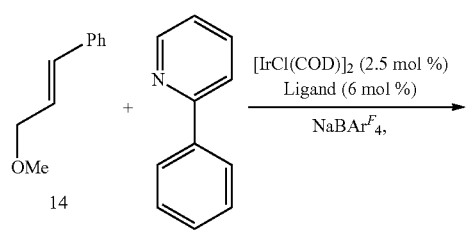

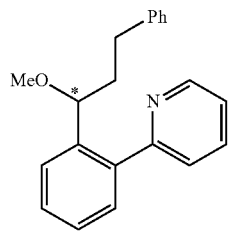

15

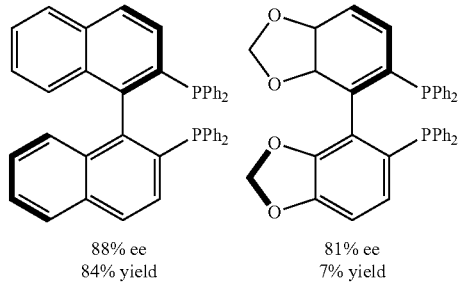

88% ee        81% ee
84% yield    7% yield

Angew. Chem. Int. Ed. 2017, 56, 5607.

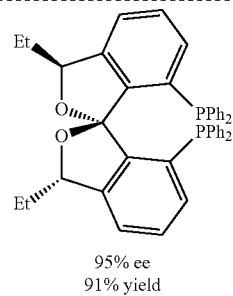

95% ee
91% yield (S,S,S)-SPIRAP

Substrate Synthesis

Alkenyl ether (14) was prepared according to Matsubara, et al., *J. Am. Chem. Soc.* 2010, 132 (20), 6880-6881. A flask was charged with a suspension of sodium hydride (NaH) (60%, prewashed with hexanes, 520 mg, 21.7 mmol) and THF (30 mL) before addition of cinnamyl alcohol (1.4 mL, 10.87 mmol). After stirring at room temperature for 100 min, methyl iodide (2.0 mL, 32.6 mmol) was added at room temperature. After 3 h, reaction mixture was filtered through a SiO$_2$ pad, with 50% EtOAc in hexanes elution. The filtrate was concentrated in vacuo and purified by FCC (SiO$_2$, 5% EtOAc in hexanes) to afford the desired product (1.52 g, 94.4% yield) as a colorless oil. $^1$H NMR (400 MHz, Chloroform-d) δ 7.38 (dd, J=8.3, 1.5 Hz, 1H), 7.31 (dd, J=8.4, 6.7 Hz, 1H), 7.26-7.20 (m, 1H), 6.28 (dt, J=16.0, 6.0 Hz, 1H), 4.09 (dd, J=6.0, 1.5 Hz, 1H), 3.38 (d, J=0.5 Hz, 2H). $^{13}$H NMR (100 MHz, cdcl$_3$) δ 136.70, 132.40, 128.52, 127.63, 126.44, 125.94, 73.07, 57.96.

Asymmetric Hydroarylation

Hydroarylations were carried out according to Ebe, et al., *Angew. Chemie Int. Ed.* 2017, 56(20), 5607-5611. Bis(1,5-cyclooctadiene)diiridium(I) dichloride (3.3 mg, 0.0049 mmol) and (S,S,S)-SPIRAP (7.6 mg, 0.012 mmol) were added to a Schlenk tube strictly under nitrogen. PhMe (330 μL) was added and the mixture was stirred at room temperature. After 20 min, sodium tetrakis[3,5-bis(trifluoromethyl)phenyl]borate (18.1 mg, 0.0196 mmol) was added. After 15 min, 2-phenylpyridine (30 μL, 0.21 mmol) and alkenyl ether 14 (30 μL, 0.196 mmol) were added. Reaction mixture was then heated to 70° C. After 24 h, reaction mixture was cooled to room temperature. Volatiles were removed in vacuo and the crude product was purified by FCC (10% EtOAc in hexanes) to obtain pure product 15 (56.9 mg, 96% yield, 95.4% ee) as colorless oil that solidifies on cooling. $^1$H NMR (401 MHz, Chloroform-d) δ 8.52 (d, J=5.0 Hz, 1H), 7.60 (m, J=8.6, 6.6 Hz, 2H), 7.43 (m, J=8.1, 5.6, 3.2 Hz, 1H), 7.34-7.28 (m, 2H), 7.23-7.08 (m, 5H), 7.08-6.98 (m, 2H), 4.40 (dd, J=8.3, 4.4 Hz, 1H), 3.14 (s, 3H), 2.71 (ddd, J=13.8, 8.3, 5.5 Hz, 1H), 2.60 (dt, J=13.7, 8.2 Hz, 1H), 1.96 (tt, J=8.2, 5.0 Hz, 2H).

Pd-Catalyzed Asymmetric Allylic Alkylation

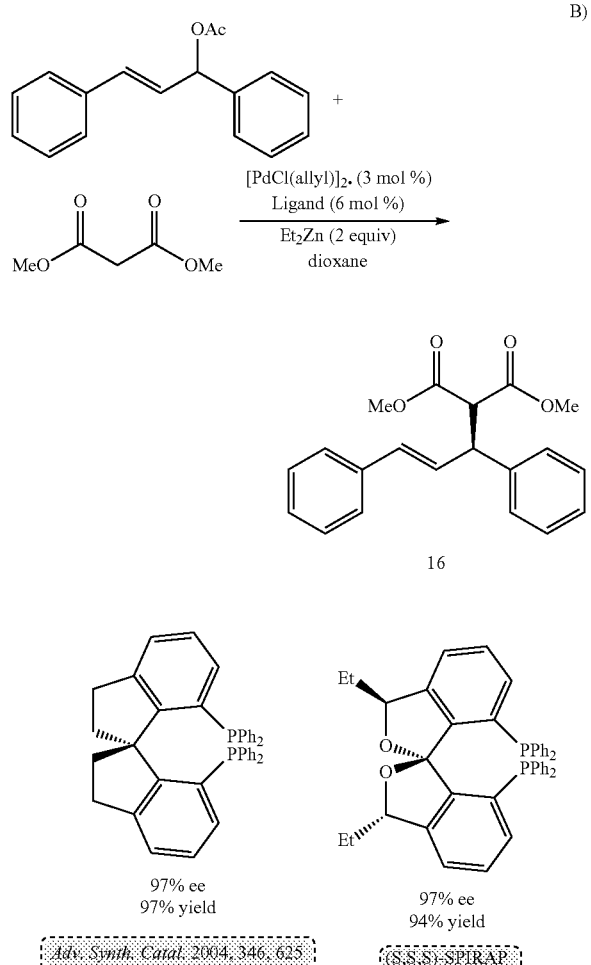

Substrate Synthesis (E)-1,3-diphenylallyl acetate was synthesized following a slightly modified as reported by Gao, et al., *RSC Adv.* 2015, 5(43), 33818-33822. (E)-chalcone (988 mg, 4.74 mmol) and methanol (12 mL) were cooled to 0° C. before portionwise addition of sodium borohydride (365 mg, 9.66 mmol). Reaction mixture was then warmed to room temperature. After 1 h, reaction mixture was partitioned between EtOAc (30 mL) and water (30 mL). After separating the layers, the aqueous solution was extracted with EtOAc twice. Combined organic was washed with brine, dried over Na$_2$SO$_4$, and concentrated in vacuo. The allylic alcohol was acetylated without further purification as follows. 4-Dimethylaminopyridine (58.8 mg, 48.1 mmol), DCM (30 mL), and triethylamine (1.7 mL, 12.2 mmol) were added to the crude. Reaction mixture was cooled to 0° C. before dropwise addition of acetic anhydride (1.1 mL, 11.6 mmol). Reaction mixture was warmed to room temperature and stirred overnight. Water (30 mL) was added, and after separating the layers, the aqueous solution was extracted with DCM twice. Combined organic layers were washed with brine, dried over Na$_2$SO$_4$, and concentrated in vacuo. Pure product (841.2 mg, 70.3% yield) was obtained after purification by FCC (SiO$_2$, 10→20% EtOAc in hexanes). $^1$H NMR (400 MHz, Chloroform-d) δ 7.49-7.13 (m, 10H), 6.65 (d, J=15.8 Hz, 1H), 6.46 (d, J=6.9 Hz, 1H), 6.36 (dd, J=15.7, 6.8 Hz, 1H), 2.15 (s, 3H). $^{13}$C NMR (100 MHz, cdcl$_3$) δ 169.97, 139.20, 136.14, 132.56, 128.59, 128.54, 128.45, 128.39, 128.29, 128.13, 128.02, 127.47, 127.01, 126.66, 76.10, 21.32.

Asymmetric Allylic Alkylation

The asymmetric alkylation was performed following a modified as reported by Xie, et. al, *Adv. Synth. Catal.* 2004, 346(6), 625-632. (E)-1,3-diphenylallyl acetate (49.3 mg, 0.195 mmol) and 1,4-dioxane (1 mL) were stirred at room temperature. In a separate flask, allylpalladium(II) chloride dimer (1.8 mg, 0.0049 mmol), (S,S,S)-SPIRAP (7.6 mg, 0.012 mmol), and 1,4-dioxane (1 mL) were stirred for 1 hour at room temperature. The catalyst solution was transferred to the substrate flask by syringe with dioxane washings (1 mL). In another flask, dimethyl malonate (45 μL, 0.39 mmol) and 1,4-dioxane (1 mL) were cooled to 0° C., and then treated with a 1 M solution of diethylzinc in hexanes (390 μL, 0.39 mmol). The substrate flask was cooled with an ice bath while the reagent solution was slowly transferred via syringe with dioxane washings (1 mL). Reaction mixture was then warmed to room temperature. After 90 min, reaction mixture was diluted with EtOAc (5 mL) and quenched with a saturated aqueous solution of NH$_4$Cl (5 mL). After separating the layers, the aqueous solution was extracted with EtOAc twice. Combined organic layers were washed with brine, dried over Na$_2$SO$_4$, and concentrated in vacuo. Crude product was purified by FCC (SiO$_2$, gradient 0→10% EtOAc in hexanes) to afford pure product 16 (59.8 mg, 94% yield, 96.6% ee) as colorless oil. $^1$H NMR (401 MHz, Chloroform-d) δ 7.36-7.16 (m, 10H), 6.48 (d, J=15.8 Hz, 1H), 6.33 (dd, J=15.7, 8.6 Hz, 1H), 4.33-4.19 (m, 1H), 3.95 (d, J=10.9 Hz, 1H), 3.71 (s, 3H), 3.52 (s, 3H).

Pd-Catalyzed Asymmetric Intermolecular Heck Reaction and Domino Cyclization

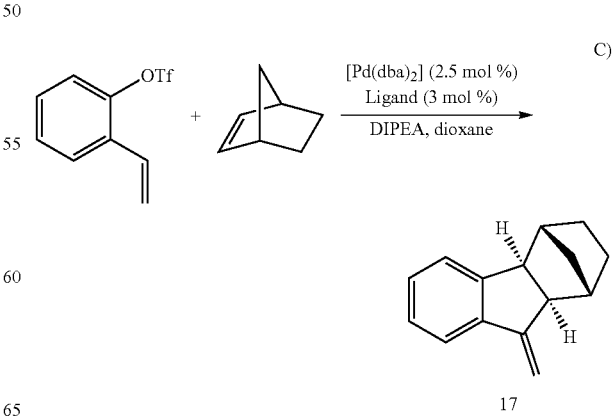

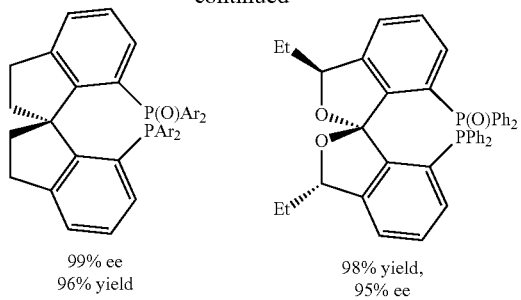

99% ee
96% yield
Angew. Chem. Int. Ed. 2013, 52, 8676

98% yield,
95% ee
(S,S,S)-SPIRAP(O)

Substrate Synthesis 2-vinylphenyl trifluoromethanesulfonate was synthesized following a two-step procedure as reported by Hu, et al., Angew. Chemie Int. Ed. 2013, 52 (33), 8676-8680. Methyl-triphenyl-phosphonium bromide (3.52 g, 9.85 mmol) and diethyl ether (60 mL) were cooled to 0° C. before the addition of potassium tert-butoxide (KOt-Bu) (2.16 g, 19.25 mmol). After 15 min, a solution of salicylaldehyde (1 mL, 9.38 mmol) in diethyl ether (30 mL) was added. Reaction mixture was then warmed to room temperature. After 16 h, a saturated aqueous solution of NH$_4$Cl (30 mL) was added. After separating the layers, the aqueous solution was extracted with diethyl ether twice. Combined organic layers were washed with brine, dried over Na$_2$SO$_4$, and concentrated in vacuo. Crude product was purified by FCC (SiO$_2$, gradient 5→15% EtOAc in hexanes) to afford unreacted starting material (141 mg, 12% recovery) and pure 2-vinyl-phenol (942 mg, 84% yield) as light yellow liquid.

Vinylphenol (767 mg, 6.38 mmol), DCM (18 mL), and pyridine (1 mL, 12.77 mmol) were cooled to 0° C. before the dropwise addition of trifluoromethanesulfonic anhydride (1.3 mL, 7.66 mmol). Reaction mixture was then warmed to room temperature. After 13 h, reaction mixture was filtered with DCM washings, concentrated in vacuo, and purified by FCC (SiO$_2$, hexanes) to afford 2-vinyltriflate (1.427 g, 89% yield) as colorless liquid. $^1$H NMR (401 MHz, Chloroform-d) δ 7.69-7.59 (m, 1H), 7.39-7.15 (m, 3H), 6.92 (dd, J=17.5, 11.1 Hz, 1H), 5.84 (d, J=17.5 Hz, 1H), 5.48 (d, J=11.0 Hz, 1H). $^{13}$C NMR (101 MHz, cdcl$_3$) δ 146.82, 131.01, 129.23, 128.81, 128.35, 127.21, 121.62, 120.15, 118.58, 116.97. $^{19}$F NMR (377 MHz, cdcl$_3$) δ −73.64.

Asymmetric Heck Reaction

The asymmetric Heck reaction was performed as follows. Bis(dibenzylideneacetone)palladium(0) (4.7 mg, 0.0082 mmol), (S,S,S)-SPIRAP(O) (6.5 mg, 0.0098 mmol) were added to a Schlenk tube strictly under nitrogen. 1,4-dioxane (320 μL) was added, and the mixture was stirred at room temperature. After 30 min, 2-vinyltriflate (60 μL, 0.32 mmol), norbornene (122.1 mg, 1.30 mmol), and diisopropylethylamine (110 μL, 0.63 mmol) were added and then the mixture was heated to 70° C. After 20 h, reaction mixture was concentrated in vacuo and purified through a short pipette column (SiO$_2$) with hexanes elution to afford pure product 17 (63.7 mg, quant.) $^1$H NMR (400 MHz, Chloroform-d) δ 7.50-7.39 (m, 1H), 7.29-7.12 (m, 3H), 5.51 (d, J=2.4 Hz, 1H), 5.03 (d, J=2.0 Hz, 1H), 3.06 (d, J=7.0 Hz, 1H), 2.83 (d, J=7.0 Hz, 1H), 2.36-2.20 (m, 2H), 1.61 (m, J=18.4, 15.4, 11.6, 5.7 Hz, 2H), 1.41 (m, J=18.9, 9.0, 2.4 Hz, 2H), 1.09-0.92 (m, 2H). $^{13}$C NMR (100 MHz, cdcl$_3$) δ 154.44, 148.89, 142.58, 128.54, 126.57, 125.09, 119.95, 102.93, 52.20, 52.01, 44.59, 42.49, 32.33, 29.36, 28.62.

Ir-Catalyzed Asymmetric Hydrogenation

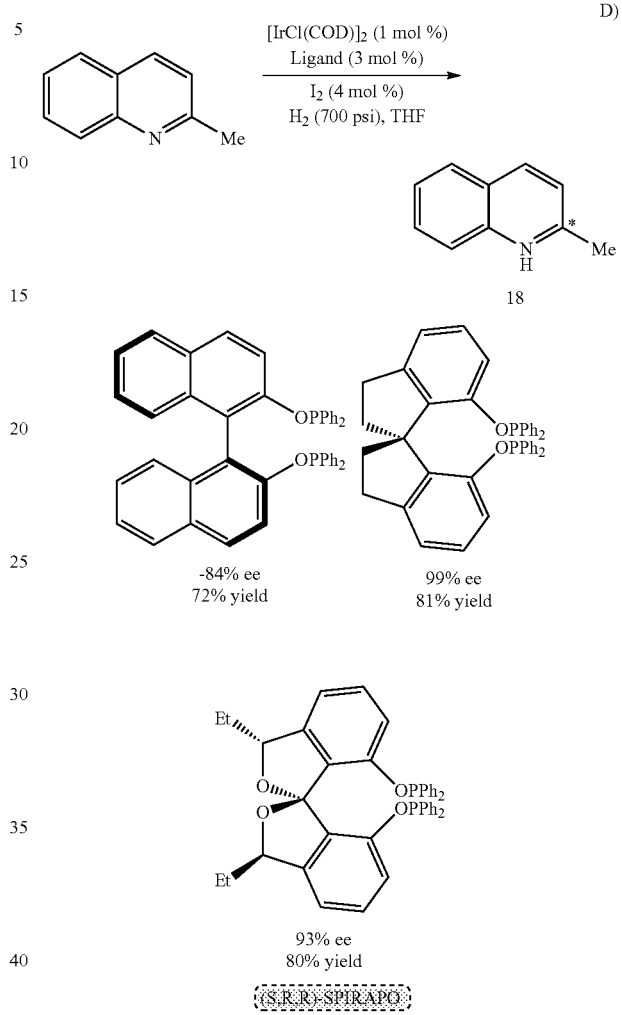

(R)-2-methyl-1,2,3,4-tetrahydroquinoline (18)

(S,R,R)-SPIRAPO-12 (6.1 mg, 0.009 mmol) and [Ir(COD)Cl]$_2$ (2.0 mg, 0.003 mmol) were measured and packed into the Schlenk tube in the glovebox before the addition of dry THF (3.0 mL) to make the stock solution. 2-methylquinoline (13.5 uL, 0.1 mmol) and I$_2$ (1.0 mg, 0.004 mmol) were added to the flask before the addition of the stock solution (1.0 mL). The reaction flask was placed into the hydrogenation apparatus before purging with N$_2$ and H$_2$, and the reaction was stirred under 700 psi H$_2$ for 20 hours. Reaction volatiles were removed in vacuo, and the crude product was purified by FCC (SiO2, 20% EtOAc in hexanes) to afford (R)-2-methyl-1,2,3,4-tetrahydroquinoline 18 (11.7 mg, 80% yield, 93% ee) as clear oil. $^1$H NMR (400 MHz, Chloroform-d) δ 7.05-6.89 (m, 2H), 6.58 (td, J=7.4, 1.2 Hz, 1H), 6.45 (dd, J=8.3, 1.2 Hz, 1H), 3.67 (br s, 1H), 3.39 (dtd, J=10.0, 6.3, 2.9 Hz, 1H), 2.94-2.63 (m, 2H), 1.96-1.81 (m, 1H), 1.67-1.49 (m, 1H), 1.19 (d, J=6.3 Hz, 3H). $^{13}$C NMR (100 MHz, cdcl$_3$) δ 144.73, 129.22, 126.64, 121.07, 116.94, 113.95, 47.12, 30.10, 26.56, 22.58.

What is claimed:

1. A compound of formula (I):

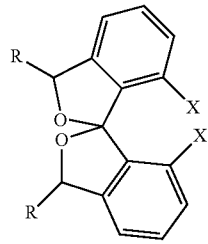

wherein each R is independently selected from the group consisting of $C_{1-8}$ alkyl, $C_{1-8}$ heteroalkyl having 1-4 heteroatoms independently selected from N, O, and S, $C_{3-6}$ cycloalkyl, 3-10 membered heterocycloalkyl having 1-4 heteroatoms independently selected from N, O, and S, $C_{6-10}$ aryl, and 5-10 membered heteroaryl having 1-4 heteroatoms independently selected from N, O, and S;

each X is independently selected from OH, $PAr_2$, $P(O)Ar_2$, $OPAr_2$, $C_{3-6}$ cycloalkyl, 3-10 membered heterocycloalkyl having 1-4 heteroatoms independently selected from N, O, and S, $C_{6-10}$ aryl, and 5-10 membered heteroaryl having 1-4 heteroatoms selected from N, O, and S, or each X together form $O_2PNR'_2$;

Ar is $C_{6-10}$ aryl; and each R' is independently selected from hydrogen and $C_{1-8}$ alkyl.

2. The compound of claim 1, wherein the compound of formula (I) is formula (IA):

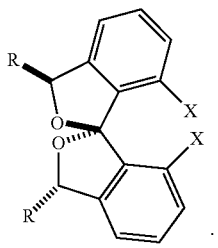

3. The compound of claim 1, wherein the compound of formula (I) has a formula (IB):

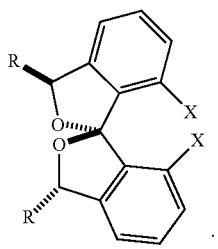

4. The compound of claim 1, wherein at least one X is OH.

5. The compound of claim 1, wherein at least one X is $PAr_2$.

6. The compound of claim 1, wherein at least one X is $OPAr_2$.

7. The compound of claim 1, wherein at least one X is $P(O)Ar_2$.

8. The compound of claim 5, wherein Ar comprises phenyl.

9. The compound of claim 1, wherein both X together form $O_2PNR'_2$.

10. The compound of claim 9, wherein R' is methyl.

11. The compound of claim 1, wherein R is ethyl.

12. The compound of claim 1, wherein at least one R is 3-10 membered heterocycloalkyl having 1-4 heteroatoms independently selected from N, O, and S.

13. The compound of claim 1 having a structure selected from the group consisting of:

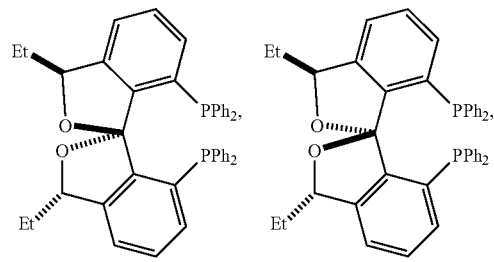

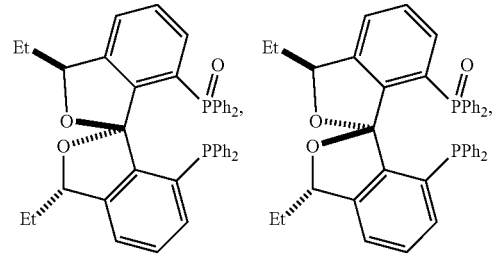

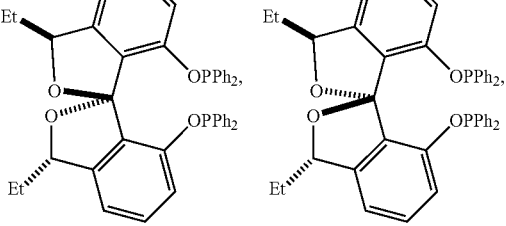

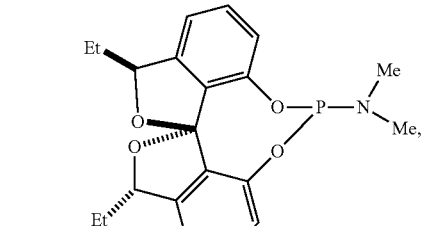

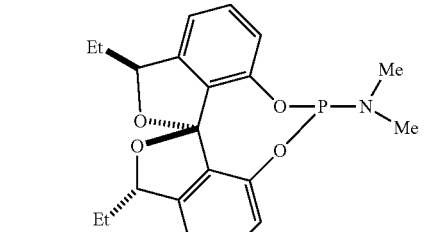

-continued

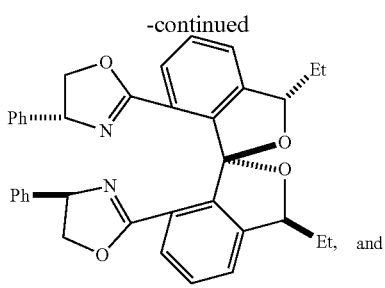

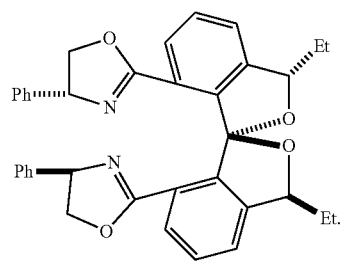

14. A catalyst comprising the compound of formula (I) according to claim 1 and a transition metal.

15. The catalyst of claim 14, wherein the transition metal comprises iridium, palladium, rhodium, platinum, copper, nickel, cobalt, or gold.

16. A method of preparing the catalyst of claim 14 comprising admixing the compound of formula (I) and the transition metal to form the catalyst.

17. The method of claim 16, wherein the transition metal comprises [Ir(COD)Cl]$_2$, [Pd(allyl)Cl]$_2$, or Pd(dba)$_2$.

18. The method of claim 16, wherein the compound of formula (I) and the transition metal are provided in a molar ratio of about 6:1 to 1:1.

19. A method comprising:
admixing a first reactant, a second reactant, and the catalyst of claim 14 under conditions sufficient to allow reaction of the first reactant and the second reactant to form a reaction product, wherein the reaction product comprises a chiral center and the reaction produces an enantiomeric excess (ee) of the reaction product.

20. The method of claim 19, wherein the reaction comprises a hydroarylation of an asymmetric alkene, an asymmetric Heck reaction, an asymmetric hydrogenation, or an allylic alcohol substitution.

21. A method of preparing compound (S,S,S)-4

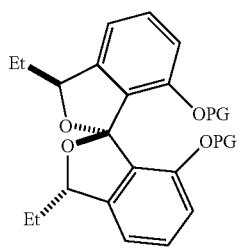

comprising
(a) cooling a solution of compound (S)-2 to 0° C.;

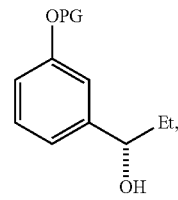

wherein PG is a hydroxy protecting group;
(b) adding an organolithium reagent to the cooled solution of step (a) to form a mixture;
(c) warming the mixture of step (b) to room temperature and keeping at room temperature to dissolve suspended material and form a solution;
(d) cooling the solution of step (c) to 0° C.;
(e) admixing the solution of step (d) and diethyl carbonate at 0° C.;
(f) warming the reaction mixture of step (e) to room temperature; and
(g) admixing the reaction mixture of step (f) with acetic acid.

22. A method of preparing compound (S,S,S)-8:

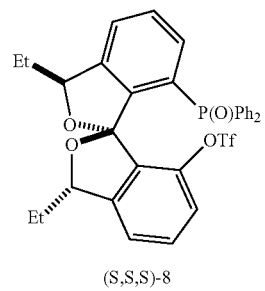

comprising:
admixing diphenylphosphine oxide with compound (S,S,S)-7 and, optionally, in the presence of compound (S,R,S)-7, in the presence of a catalyst to form compound (S,S,S)-8

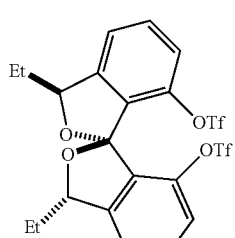

-continued
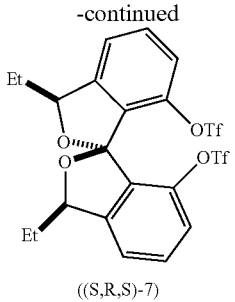
((S,R,S)-7)
wherein the temperature of the admixing is 70° C. to 90° C.
23. A method of preparing compound (R,S,S)-8:
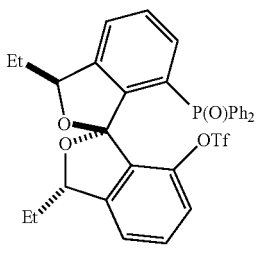
(R,S,S)-8
comprising:
admixing diphenylphosphine oxide with compound (R,S,S)-7 in the presence of a catalyst to form compound (R,S,S)-8:
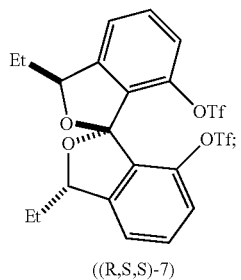
((R,S,S)-7)
wherein the temperature of the admixing is 90° C. to 110° C.
24. The compound of claim 1, wherein at least one X comprises 4-phenyl-4,5-dihydrooxazole.
* * * * *